(12) United States Patent
Endoh et al.

(10) Patent No.: US 9,355,297 B2
(45) Date of Patent: May 31, 2016

(54) BIOMETRIC INFORMATION INPUT APPARATUS AND BIOMETRIC INFORMATION INPUT METHOD

(71) Applicant: FUJITSU LIMITED, Kawasaki-shi, Kanagawa (JP)

(72) Inventors: Toshio Endoh, Yokohama (JP); Takashi Shinzaki, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 44 days.

(21) Appl. No.: 14/080,003

(22) Filed: Nov. 14, 2013

(65) Prior Publication Data

US 2014/0286528 A1 Sep. 25, 2014

(30) Foreign Application Priority Data

Mar. 19, 2013 (JP) ................................. 2013-056970

(51) Int. Cl.
*G06K 9/00* (2006.01)
*A61B 5/117* (2016.01)
*A61B 5/00* (2006.01)

(52) U.S. Cl.
CPC ............ *G06K 9/00067* (2013.01); *A61B 5/004* (2013.01); *A61B 5/117* (2013.01)

(58) Field of Classification Search
None
See application file for complete search history.

(56) References Cited

U.S. PATENT DOCUMENTS

| | | | | |
|---|---|---|---|---|
| 5,528,355 A | * | 6/1996 | Maase | G07C 9/00158 356/71 |
| 8,787,624 B2 | * | 7/2014 | Hama et al. | 382/115 |
| 2004/0189829 A1 | * | 9/2004 | Fukuda | H04N 5/23222 348/239 |
| 2005/0148876 A1 | * | 7/2005 | Endoh | A61B 5/117 600/454 |

(Continued)

FOREIGN PATENT DOCUMENTS

| | | |
|---|---|---|
| JP | 09-102046 | 4/1997 |
| JP | 2002-329205 | 11/2002 |

(Continued)

OTHER PUBLICATIONS

EESR—Extended European Search Report dated Jun. 24, 2014 issued with respect to the corresponding European Application No. 13192287.4.

(Continued)

*Primary Examiner* — Utpal Shah
*Assistant Examiner* — Samah Beg
(74) *Attorney, Agent, or Firm* — Fujitsu Patent Center

(57) ABSTRACT

A biometric information input apparatus includes an image capturing section configured to obtain a captured image of a biological object; a pliable part detecting section configured to detect whether there is a pliable part on a surface of the biological object by obtaining a distance to the surface of the biological object from the captured image and comparing the obtained distance with a predetermined distance to be compared set beforehand; and an extracting section configured to extract biometric information from the captured image if the pliable part is not detected by the pliable part detecting section.

9 Claims, 14 Drawing Sheets

(56) References Cited

U.S. PATENT DOCUMENTS

| | | | |
|---|---|---|---|
| 2005/0162420 A1* | 7/2005 | Ban et al. ....................... 345/419 |
| 2007/0098223 A1 | 5/2007 | Kamata et al. |
| 2007/0160263 A1* | 7/2007 | Abiko et al. ................... 382/115 |
| 2008/0137920 A1* | 6/2008 | Miura ................ G06K 9/00013 |
| | | | 382/124 |
| 2008/0180406 A1* | 7/2008 | Han .................... G06F 3/04883 |
| | | | 345/173 |
| 2008/0226136 A1 | 9/2008 | Takaku et al. |
| 2008/0309662 A1* | 12/2008 | Hassner et al. ............... 345/419 |
| 2009/0003671 A1* | 1/2009 | Inoue et al. ................... 382/128 |
| 2010/0127827 A1* | 5/2010 | Watanabe .......... G06K 9/00114 |
| | | | 340/5.83 |
| 2010/0215257 A1* | 8/2010 | Dariush ................... G06K 9/48 |
| | | | 382/159 |
| 2010/0280399 A1* | 11/2010 | Francis .............. A61B 5/04011 |
| | | | 600/509 |
| 2012/0133580 A1* | 5/2012 | Kirby ...................... G06F 3/017 |
| | | | 345/156 |
| 2013/0027184 A1* | 1/2013 | Endoh ......................... 340/5.83 |
| 2013/0308834 A1* | 11/2013 | Suzuki et al. .................. 382/115 |
| 2014/0020090 A1* | 1/2014 | Nada et al. ....................... 726/19 |
| 2014/0294261 A1* | 10/2014 | Abe ............................... 382/124 |
| 2015/0035961 A1* | 2/2015 | Chen et al. ....................... 348/77 |
| 2015/0268728 A1* | 9/2015 | Makela .................. G06F 3/017 |
| | | | 345/156 |

FOREIGN PATENT DOCUMENTS

| | | |
|---|---|---|
| JP | 2004-297223 | 10/2004 |
| JP | 2007-213199 | 8/2007 |
| JP | 2012-155405 | 8/2012 |
| JP | 2012-518856 | 8/2012 |
| WO | 2004-021884 | 3/2004 |
| WO | 2010-099034 | 9/2010 |

OTHER PUBLICATIONS

Ruo Zhang et al., "Shape from Shading: A Survey", IEEE Transactions on Pattern Analysis and Machine Intelligence, vol. 21, No. 8, Aug. 1999, pp. 690-706.

* cited by examiner

FIG.12E DROPPED FINGERS
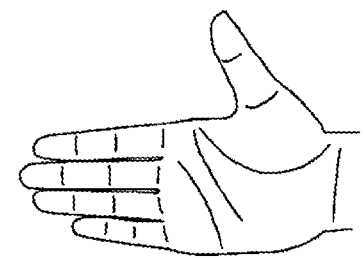
FIG.12D CLOSED FINGERS (WITHOUT THUMB)
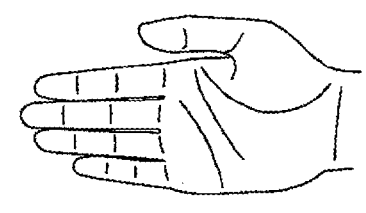
FIG.12C CLOSED FINGERS (WITH THUMB)
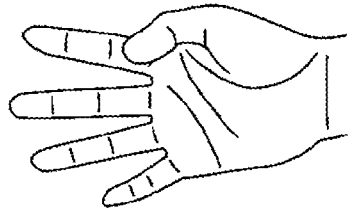
FIG.12B SELF HIDDEN
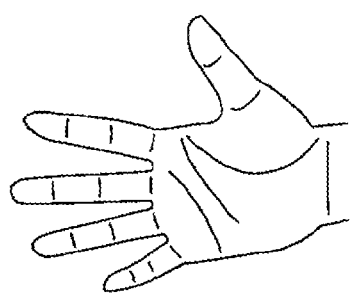
FIG.12A APPROPRIATE

| POSTURE OF OPENING HAND | CANDIDATE PLIABLE PARTS |
|---|---|
| CLOSED FINGERS (WITH THUMB) | INDEX FINGER SIDE OF THENAR |
| CLOSED FINGERS (WITHOUT THUMB) | JOINING PART OF CLOSED FINGERS |
| DROPPED FINGERS | BASE OF DROPPED FINGER |

BIOMETRIC INFORMATION INPUT APPARATUS AND BIOMETRIC INFORMATION INPUT METHOD

CROSS-REFERENCE TO RELATED APPLICATIONS

This application is based upon and claims the benefit of priority of the prior Japanese Priority Application No. 2013-056970 filed on Mar. 19, 2013, the entire contents of which are hereby incorporated by reference.

FIELD

The disclosures herein generally relate to a biometric information input apparatus, a biometric information input program, and a biometric information input method.

BACKGROUND

There exists a biometric authentication technology that uses personal biometric information such as hand veins, a fingerprint, an iris, a face or the like, as an authentication method of a person who is entering or leaving a room, a facility or the like, without human intervention. Authentication using biometric information has an advantage over authentication using a magnetic card or a personal identification number (PIN) in that it does not need to care about loss and fraudulent use.

For example, basic vein authentication starts with illuminating near infrared light onto a part (for example, a palm) of a human body where an image of veins can be easily captured, captures strength distribution of reflected or transmitted light, and extracts the image of veins (blood vessels) by characteristic extraction based on the strength distribution. Also, vein authentication verifies the extracted image of veins (called "data to be verified", hereafter) with the image of veins of the person registered in advance (called "registered data", hereafter) to determine whether they are coincident with each other, and outputs an authentication result.

Here, swell (concavity and convexity) of muscles at the base of fingers change depending on the form of the fingers when the image is captured, such as open fingers, closed fingers, or bent fingers. In the following, the swell part is called a "pliable part". At a pliable part, it is difficult to extract a satisfactory image of veins because near infrared light used for capturing an image is illuminated on the surface of skin obliquely and the light is scattered due to thickness inside of skin and muscle, which degrades authentication precision.

Conventionally, there exist methods to cope with the above problem such as a method of providing a guiding mechanism to instruct a hand posture for opening a palm, a method of detecting a degree of openness of a palm to guide a user to take a posture suitable for authentication, and a method of capturing images of a palm repeatedly so that the most suitable image for authentication can be selected (see, for example, Patent Documents 1 to 4).

RELATED-ART DOCUMENTS

Patent Documents

[Patent Document 1] WO 2004/021884
[Patent Document 2] Japanese Laid-open Patent Publication No. 09-102046
[Patent Document 3] Japanese Laid-open Patent Publication No. 2004-297223
[Patent Document 4] Japanese Laid-open Patent Publication No. 2012-155405

However, if providing a guiding mechanism for instructing the hand posture, the image capturing device becomes large and additional efforts are imposed on a user, which reduce convenience. Also, if guiding a user to open the palm, additional efforts are imposed on the user, which reduces convenience. Also, if capturing images repeatedly to select the most suitable image for authentication is required, time for capturing images increases, which reduces convenience.

SUMMARY

According to at least one embodiment of the present invention, a biometric information input apparatus includes an image capturing section configured to obtain a captured image of a biological object; a pliable part detecting section configured to detect whether there is a pliable part on a surface of the biological object by obtaining a distance to the surface of the biological object from the captured image and comparing the obtained distance with a predetermined distance to be compared set beforehand; and an extracting section configured to extract biometric information from the captured image if the pliable part is not detected by the pliable part detecting section.

The object and advantages of the embodiment will be realized and attained by means of the elements and combinations particularly pointed out in the claims. It is to be understood that both the foregoing general description and the following detailed description are exemplary and explanatory and are not restrictive of the invention as claimed.

BRIEF DESCRIPTION OF DRAWINGS

FIG. 12A-12E are schematic views illustrating an example of postures of a palm;

DESCRIPTION OF EMBODIMENTS

In the following, embodiments of the present invention will be described with reference to the drawings.

<First Embodiment of Biometric Information Input Authentication System>

Figure 1:
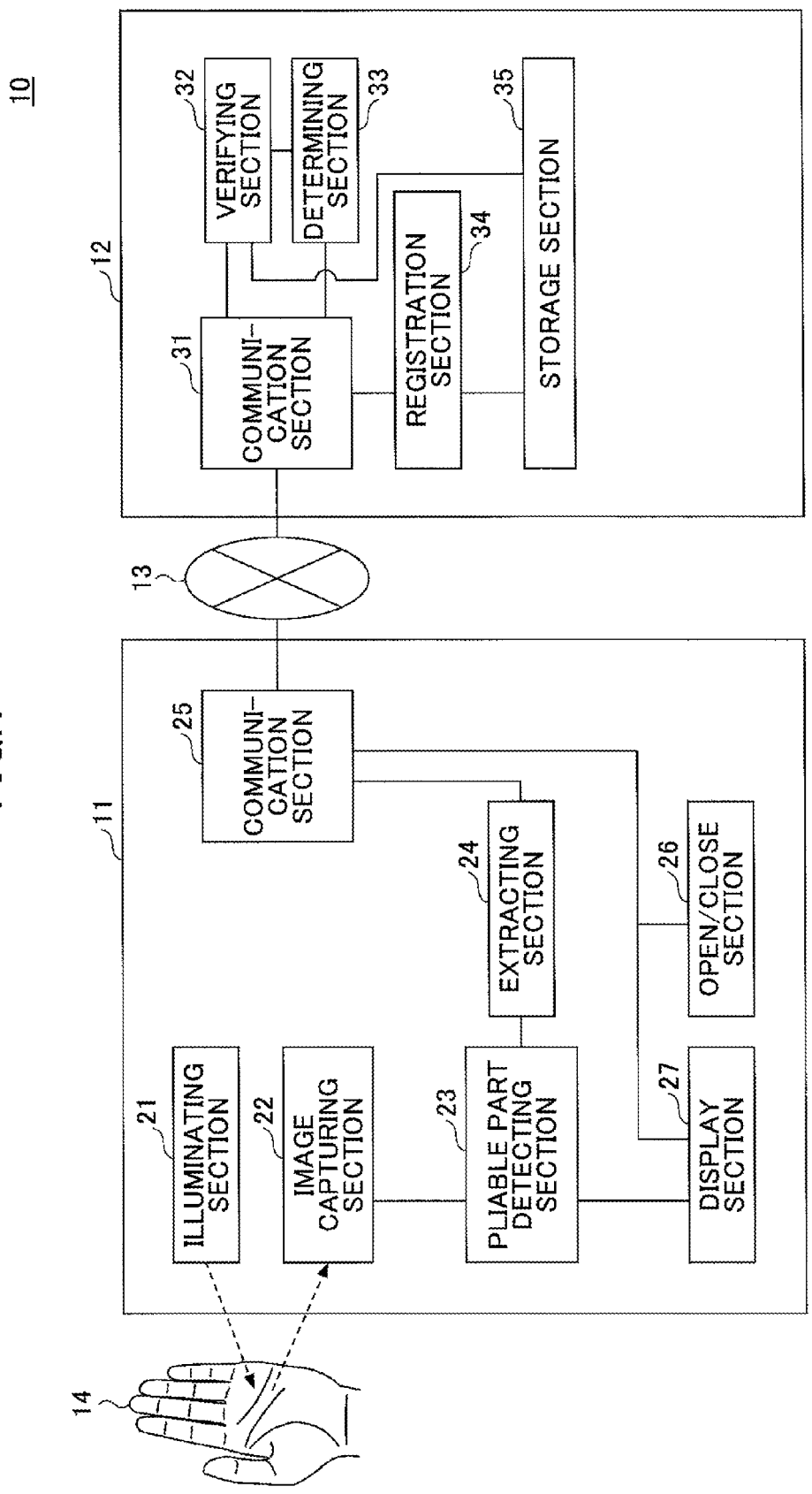
FIG. 1 is a schematic view illustrating an example of a biometric information input authentication system according to a first embodiment.

FIG. 1 is a schematic view illustrating an example of a biometric information input authentication system according to the first embodiment. The biometric information input authentication system 10 illustrated in FIG. 1 includes a biometric information input apparatus 11 and an authentication apparatus 12. The biometric information input apparatus 11 and the authentication apparatus 12 are connected with each other via a communication network 13 so that they are in a state in which data can be transmitted and received, but the configuration is not limited to this, for example, functions of the authentication apparatus 12 may be configured to be included in the biometric information input apparatus 11 as one united apparatus. In this case, the authentication apparatus 12 may be considered as the authentication section in the biometric information input apparatus 11.

Although the biometric information input authentication system 10 illustrated in FIG. 1 is a system, for example, that uses veins of a palm 14 of a user, as an example of biometric information, and authenticates the user when opening or closing a door of a predetermined room or a facility when entering or leaving, but it is not limited to this. For example, according to the first embodiment, although a part of a human body such as a hand (palm), a face, an eye or the like as a biological object can be used for obtaining biometric information such as an image of veins, a fingerprint, wrinkles, an iris or the like, but it is not limited to these.

In the biometric information input authentication system 10 illustrated in FIG. 1, the biometric information input apparatus 11 includes an illuminating section 21, an image capturing section 22, a pliable part detecting section 23, an extracting section 24, a communication section 25, an open/close section 26, and a display section 27.

The illuminating section 21 illuminates predetermined light (for example, near infrared light having a wavelength set beforehand) onto a palm 14, which is an example of a biological object, for obtaining an image of hand veins (biometric information). The illuminating section 21 may include a sensor or the like for detecting that a hand of a user enters into an illumination area, and illuminates the predetermined light onto the predetermined area at a timing detected by the sensor.

The image capturing section 22 captures an image of the palm 14 illuminated with the predetermined light by the illuminating section 21. The image capturing section 22 captures, for example, strength distribution of the near infrared light reflected or transmitted at the palm 14 illuminated by the illuminating section 21.

A unified image capturing unit may be provided that combines the illuminating section 21 and the image capturing section 22 described above according to the first embodiment. Also, according to the first embodiment, vein authentication of a palm 14 is carried out by noncontact or light contact with a part of the palm 14 without rigidly fixing the palm 14 on the image capturing unit for reducing psychological resistance of a user and making the image capturing unit smaller.

Figure 2:
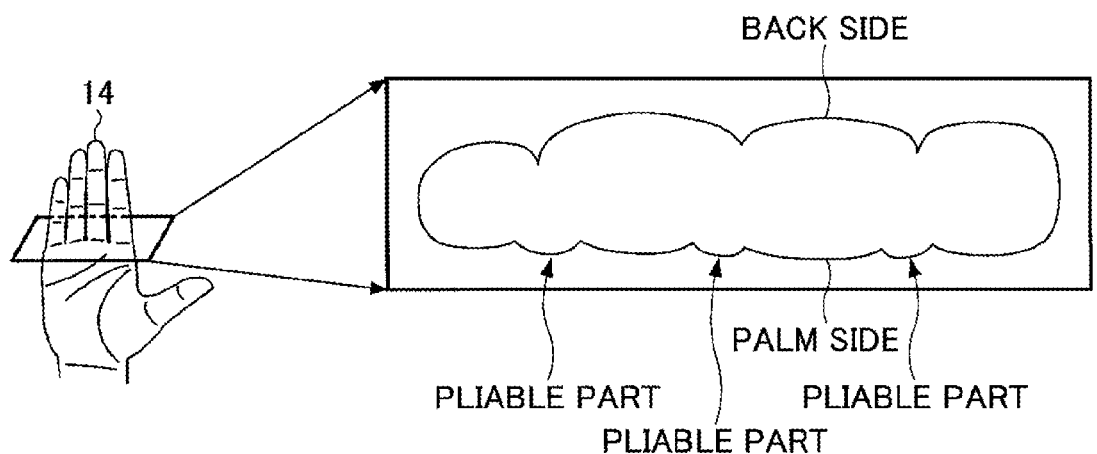
FIG. 2 is a schematic view illustrating pliable parts on the surface of a palm.

The pliable part detecting section 23 detects a pliable part on the surface of a palm 14. FIG. 2 is a schematic view illustrating pliable parts on the surface of a palm 14. In the example in FIG. 2, a cross-sectional surface around the base of four fingers without the thumb is illustrated. As illustrated in FIG. 2, the forms of surface areas between the fingers have swell (concavity and convexity) on the palm side surface, for example, when closing fingers. As the surface areas are pliable due to the concavity and convexity, light reflected at veins when capturing an image attenuates due to skin and muscle thickness and the light scatters because it is not perpendicular to the surface, which degrades precision when inputting an image of veins. Therefore, the pliable part detecting section 23 detects whether there is a "pliable part" as illustrated in FIG. 2. If the pliable part detecting section 23 detects a pliable part, it may compensate the image for the pliable part or output a message that prompts the user to open fingers for capturing the image again.

The extracting section 24 extracts biometric information such as an image of veins or the like by executing characteristic extraction on the image of the palm 14 captured by the image capturing section 22. Here, content extracted by the extracting section 24 is not limited to an image of veins, but may be, for example, a palm print, wrinkles or the like, or may be a combination of these.

The communication section 25 transmits information (for example, vein information) or the like extracted by the extracting section 24 to the authentication apparatus 12 via the communication network 13, for example, for executing authentication. At this moment, the communication section 25 may transmit an authentication request to the authentication apparatus 12 for having the authentication apparatus 12 execute authentication with the information extracted by the extracting section 24 as data to be verified. Also, the communication section 25 may transmit a registration request to the authentication apparatus 12 for having the authentication apparatus 12 register the information extracted by the extracting section 24 as data to be registered.

The communication section 25 receives an authentication result after verification, a registration or the like obtained by the authentication apparatus 12. The communication section 25 outputs the authentication result to the open/close section 26, the display section 27 and the like, or outputs a registration result to the display section 27.

The open/close section 26 opens or closes a door based on an authentication result determined by the authentication apparatus 12. For example, the open/close section 26 opens the door for a predetermined period of time if a positive authentication result is obtained in that the data to be verified coincides with one of the images of veins registered beforehand. Also, the open/close section 26 may close the door when a predetermined period of time (for example, five seconds) has passed after opening the door.

The display section 27 displays an image captured by the image capturing section 22, displays a pliable part detection result or the like detected by the pliable part detecting section 23, and displays an authentication result by the authentication apparatus 12 or the like. The display section 27 is, for example, a display unit, a monitor, a touch panel or the like, but not limited to these.

Here, the communication section 25 described above is an example of an output section for outputting information externally, and the display section 27 is, for example, an example of the output section for outputting information to a user via a display or the like.

In the biometric information input authentication system 10 illustrated in FIG. 1, the authentication apparatus 12 includes a communication section 31, a verifying section 32, a determining section 33, a registration section 34, and a storage section 35.

The communication section 31 outputs an authentication request and data to be verified transmitted from the communication section 25 of the biometric information input apparatus 11 via the communication network 13 or the like to the verifying section 32. Also, the communication section 31 outputs data to be registered to the registration section 34 based on a registration request from the biometric information input apparatus 11 when registering newly registered data into the storage section 35.

The verifying section 32 verifies information to be authenticated (for example, an image of veins) obtained, for example, from the biometric information input apparatus 11 with authentication information of registered people (users) stored in the storage section 35, to determine whether the information to be authenticated coincides with one of the registered people. The verifying section 32 outputs a verification result obtained by verification described above to the determining section 33.

The determining section 33 executes a determination procedure based on a verification result. Here, when determining whether the images of veins coincide with each other, it is necessary to allow a certain degree of fluctuation of the images because biometric information including the images of veins may fluctuate even for an individual person. Thereupon, the determining section 33 calculates a degree of similarity between data to be verified and registered data to determine a person in question is a registered one (a granted user for whom a door can be opened) if the calculated degree of similarity is greater than a threshold value set beforehand.

The determining section 33 outputs a determination result to the communication section 31 to have the communication section 31 transmit the result to the biometric information input apparatus 11. Also, the determining section 33 may store a determination result described above into the storage section 35.

The registration section 34 registers authentication information used for verification (registered data) of a user to be granted (registered person) into the storage section 35 beforehand along with identification information (user ID) of the user. Here, the authentication information is not limited to an image of veins, but may be, for example, a fingerprint, an iris or the like. Also, the registration section 34 may register multiple pieces of authentication information for each user. By combining multiple pieces of authentication information when executing authentication, authentication precision can be improved.

The storage section 35 is, for example, a memory, a hard disk or the like, but not limited to these. The storage section 35 stores biometric information (for example, an image of veins) of a user as registered data. The registered data may be stored into, for example, an IC (Integrated Circuit) card owned by a user, a database server or an external storage device, or the like. The verifying section 32 and the determining section 33 can execute authentication by referring to the registered data stored into the IC card described above or the external storage device when necessary during authentication.

The communication network 13 is, for example, the Internet, a local area network (LAN) or the like, but not limited to these. Also, the communication network 13 may be wired or wireless, or a combination of these.

According to the first embodiment, by executing pliable part detection described above, it is possible to input biometric information more appropriately. According to the first embodiment, authentication of a palm or the like can be executed without loosing convenience even if a palm is not opened sufficiently.

<Hardware Configuration Example>

By installing an execution program (biometric information input program) that is capable of having a computer execute the above functions into a general-purpose device, for example, a personal computer (PC) or the like, it is possible to implement a biometric information input procedure according to the first embodiment. Here, a hardware configuration example of a computer will be described that can implement the biometric information input according to the first embodiment.

Figure 3:
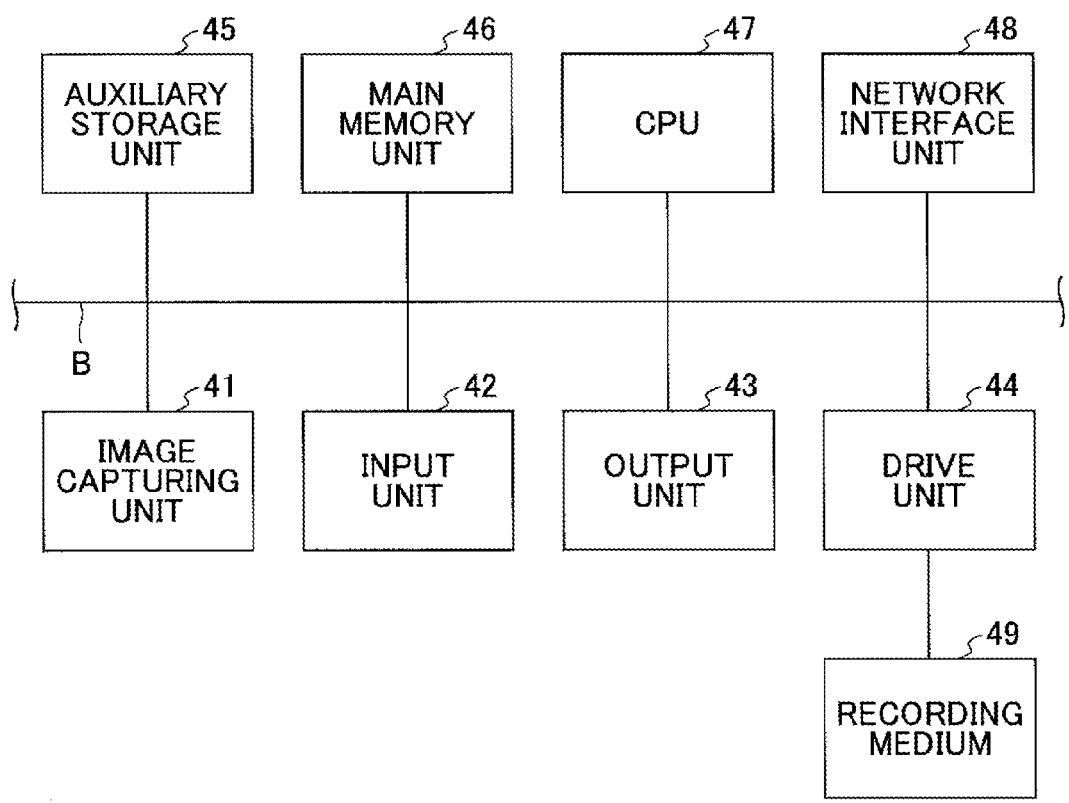
FIG. 3 is a schematic view illustrating an example of a hardware configuration with which a biometric information input procedure can be implemented.

FIG. 3 is a schematic view illustrating an example of a hardware configuration with which the biometric information input procedure can be implemented. A main body of a computer in FIG. 3 is configured to include an image capturing unit 41, an input unit 42, an output unit 43, a drive device 44, an auxiliary storage unit 45, a main memory unit 46, a central processing unit (CPU) 47 for executing various control, and a network interface unit 48, and these units are mutually connected with each other via a system bus B.

The image capturing unit 41 illuminates near infrared light or the like onto a predetermined part (for example, a palm) of a user to capture an image of the part for obtaining biometric information described above (for example, an image of veins or the like) of the user. The image capturing unit 41 includes, for example, the illuminating section 21 and the image capturing section 22 described above. The illuminating section 21 is, for example, a light emitting diode (LED) or the like that emits near infrared light. Also, the image capturing section 22 is, for example, a complementary metal oxide semiconductor (CMOS) camera, a charge coupled device (CCD) camera or the like that has a filter for cutting visible light (visible light cutting filter) or the like attached. The image capturing unit 41 is externally attached, for example, to a PC or the like, but not limited to this.

The input unit 42 includes a keyboard, a pointing device such as a mouse or the like, and a voice input device such as a microphone operated by a user or the like to receive as input an execution command of a program from the user or like, various operation information, information for activating software or the like, and the like.

The output unit 43 includes a display for displaying various windows, data and the like to operate the main body of the computer to execute processing according to the first embodiment, and displays an execution report and result or the like of a program by a control program held by the CPU 47.

Here, an execution program installed into the main body of the computer according to the first embodiment is provided, for example, with a portable recording medium 49 such as a universal serial bus (USB) memory, a CD-ROM, a DVD or the like. A recording medium 49 that records the program may be set to the drive device 44 to be installed into the auxiliary storage unit 45 via the drive device 44 from the recording medium 49 based on a control signal from the CPU 47.

The auxiliary storage unit 45 is for example, a storage section such as a hard disk drive, a solid state drive (SSD) or the like. The auxiliary storage unit 45, based on a control signal from the CPU 47, stores the execution program according to the first embodiment, a control program held in the computer, registered data used for authentication, and the like, which can be input or output when necessary. The auxiliary storage unit 45, based on a control signal from the CPU 47, reads or writes required information from or to the stored information.

The main memory unit 46 stores the execution program and the like read from the auxiliary storage unit 45 by the CPU 47. The main memory unit 46 is a read-only memory (ROM), a random access memory (RAM) and the like.

The CPU 47, based on a control program such as an operating system or the like and the execution program stored in the main memory unit 46, executes various calculations, inputs and outputs data to/from the hardware units, and controls the computer as a whole to implement various processing. Various information or the like required for an execution of a program may be obtained from the auxiliary storage unit 45, and an execution result and the like may be stored.

Specifically, the CPU 47, based on an execution direction or the like of a program obtained from the input unit 42, for example, runs the program installed in the auxiliary storage unit 45 by loading the program into the main memory unit 46.

For example, by executing the biometric information input program, the CPU 47 executes the procedures described above for illumination of near infrared light by the illuminating section 21, image capturing by the image capturing section 22, pliable part detection by the pliable part detecting section 23, extraction by the extracting section 24, communication by the communication section 25, opening and closing by the open/close section 26, displaying by the display section 27, and the like. Also, by executing the biometric information input program, the CPU 47 may execute the procedures for authentication described above including verification by the verifying section 32, determination by the determining section 33, registration by the registration section 34 and the like. Contents of processing by the CPU 47 are not limited to these. Contents executed by the CPU 47 may be stored into the auxiliary storage unit 45 if necessary.

The network interface unit 48, based on a control signal from the CPU 47, establishes a connection with a communication network or the like to obtain the execution program, software, setting information, and the like from an external device or the like connected with the communication network. Also, the network interface unit 48 may obtain a captured image of a biological object from the external device connected with the communication network. The network interface unit 48 can provide an execution result obtained by executing a program or the execution program itself to an external device or the like.

With the hardware configuration described above, it is possible to execute the biometric information input procedure according to the first embodiment. Also, by installing the program, the biometric information input procedure can be easily implemented on a general-purpose PC or the like according to the first embodiment.

<Example of Biometric Information Input Procedure According to First Embodiment>

Figure 4:
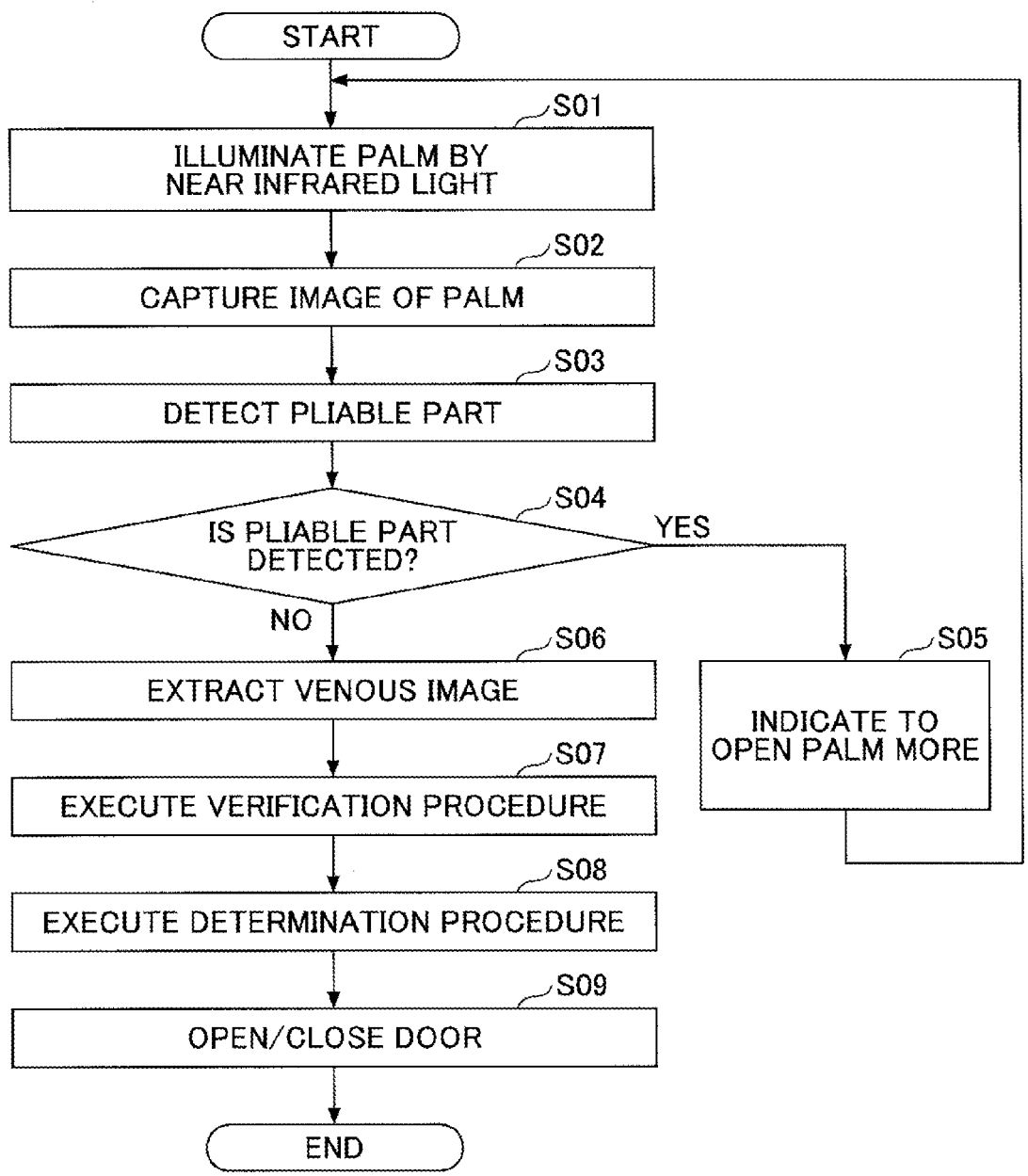
FIG. 4 is a flowchart illustrating an example of a biometric information input procedure according to the first embodiment.

An example of the biometric information input procedure will be described according to the first embodiment using a flowchart. FIG. 4 is the flowchart illustrating an example of the biometric information input procedure according to the first embodiment. Here, the biometric information input procedure illustrated in the example in FIG. 4 is a procedure used for the biometric information input authentication system 10 installed in the neighborhood of a door of a room for opening or closing the door automatically, for example, for a user who wants to enter or leave the room, which includes an authentication procedure using biometric information input by the user. Also, in the example in FIG. 4, as an example of biometric information received as input, an image of veins of a hand is assumed.

If a user holds a hand over the illuminating section 21 or the image capturing section 22 of the biometric information input apparatus 11, the illuminating section 21 illuminates near infrared light onto the palm (Step S01). The image capturing section 22 captures an image of the palm illuminated by the near infrared light (Step S02). At Steps S01 and S02 when capturing an image of the palm, identification information (ID) of the user may be received by an input section or the like such as an IC card, a keyboard or the like.

Next, the pliable part detecting section 23 detects a pliable part of the palm on the image obtained by the image capturing section 22 (Step S03), and determines whether a pliable part is detected (Step S04). If a pliable part of the palm is detected (Step S04, YES), the pliable part detecting section 23 indicates to the user to open the palm more with an error message (Step S05) via, for example, the display section 27, and the procedure goes back to Step S01 to capture an image again. At Step S05, the pliable part detecting section 23 may have the display section 27 indicate more specifically to open spaces between fingers, and indicate positional information of a location where a pliable part has been detect. Also, if a pliable part has been detected, for example, the pliable part detecting section 23 may flash a lamp or output sound with a buzzer.

At Step S04, if a pliable part of the palm is not detected (S04, NO), the extracting section 24 extracts an image of veins of the hand, which is an example of biometric information (Step S06). The extracted image of veins is transmitted to the authentication apparatus 12 via the communication section 25.

The verifying section 32 of the authentication apparatus 12 executes verification using the extracted image of veins (Step S07). At Step S07, a degree of similarity is calculated between the image of veins (data to be verified) obtained from the biometric information input apparatus 11 and the image of veins (registered data) stored in the storage section 35 beforehand. A greater degree of similarity indicates that the images are more analogous. Also, at Step S07, if the ID of the user or the like is specified, an image of veins associated with the ID is extracted among the images of veins stored in the storage section 35, and the degree of similarity is calculated using the extracted image of veins. Also, if the ID or the like is not specified, all images of veins stored in the storage section 35 are referred to for verification.

Next, the determining section 33 determines whether authentication succeeds based on the verification result (Step S08). The determining section 33, for example, determines whether the degree of similarity calculated by the verifying section 32 is greater than a threshold value set beforehand, and if the degree of similarity is greater than the threshold value, determines that authentication succeeds, or if the degree of similarity is less than or equal to the threshold value, determines that authentication fails, but not limited to these. The determination result obtained at Step S08 is transmitted to the biometric information input apparatus 11 via the communication section 31.

The open/close section 26 of the biometric information input apparatus 11 opens or closes the door based on the determination result obtained at Step S08 (Step S09). For example, if the person in question is determined as one of the registered persons, the open/close section 26 opens the door. At this moment, the display section 27 may display a successful authentication result on a screen to indicate the result to the user. Also, if the person in question is determined as a non-registered person, the display section 27 may display a failed authentication result to indicate the result to the user. Also, the open/close section 26 may execute a closing operation of the door after a predetermined period of time has passed after the opening of the door.

In the example in FIG. 4, although the description assumes that registered data is stored beforehand for authentication with input biometric information, the registration procedure may be executed for registering input biometric information as registered data. An example of the registration procedure will be described below.

<Example of Registration Procedure>

Figure 5:
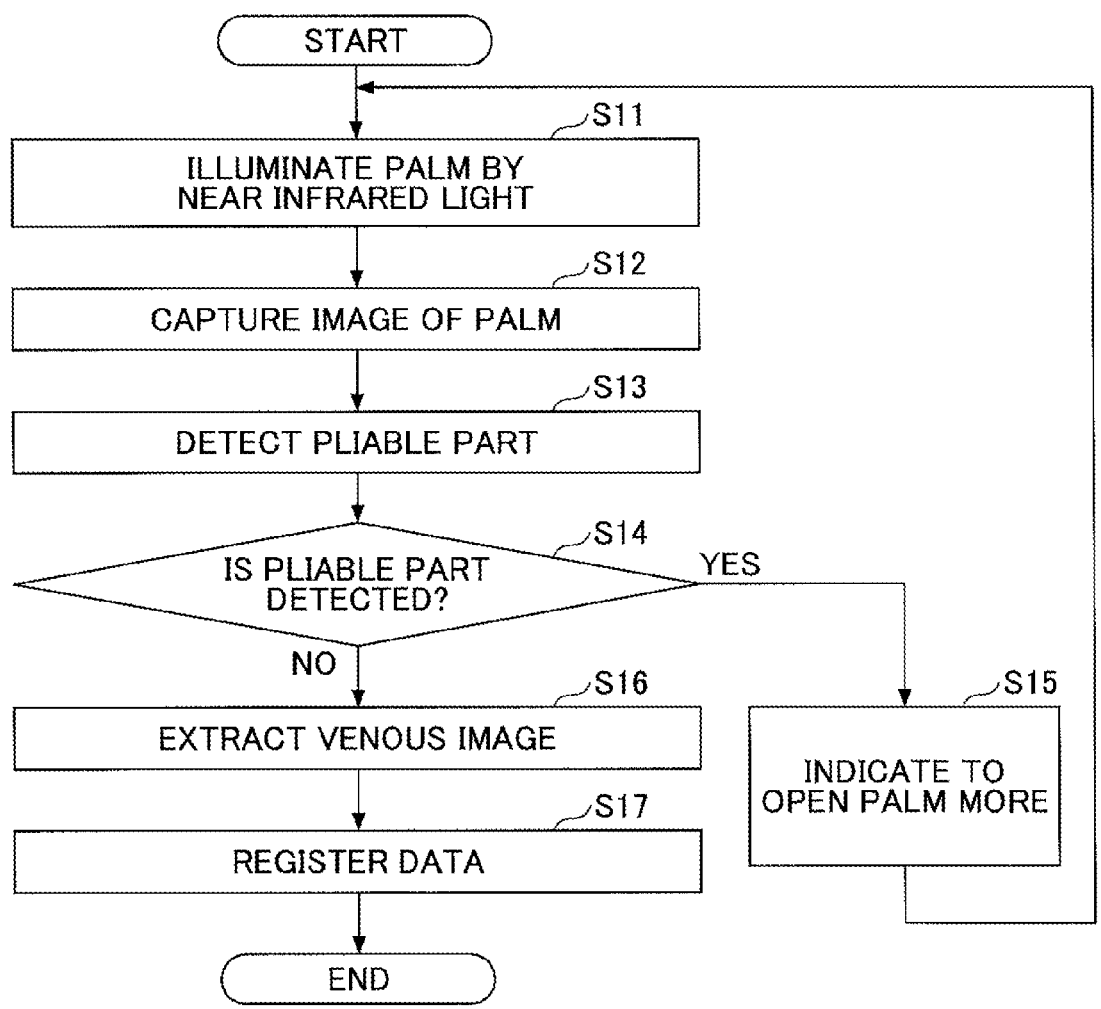
FIG. 5 is a flowchart illustrating an example of a registration procedure.

FIG. 5 is a flowchart illustrating an example of a registration procedure. In the registration procedure illustrated in the example in FIG. 5, Steps S11-S16 are the same as Steps S01-S06 in FIG. 4 described above, and their concrete description is omitted here.

In the registration procedure illustrated in FIG. 5, if a pliable part is not detected by the pliable part detecting section 23 (Step S14, NO), the extracting section 24 extracts an image of veins of a hand (Step S16). The extracted image of veins is transmitted to the authentication apparatus 12 via the communication section 25. At this moment, the identification information (user ID) of a person to be registered (a user wants to be registered) is transmitted and associated with the image.

The registration section 34 of the authentication apparatus 12 stores the user ID of the registering person and the image of veins or the like associated with the user ID into the storage section 35 to register the data (Step S17). Here, the image of veins may be stored into a storage section or the like provided in the biometric information input apparatus 11.

Next, concrete examples of the functions used in the first embodiment will be described.

<Example of Obtaining Biometric Information Using Illuminating Section 21 and Image Capturing Section 22>

Figure 6A:
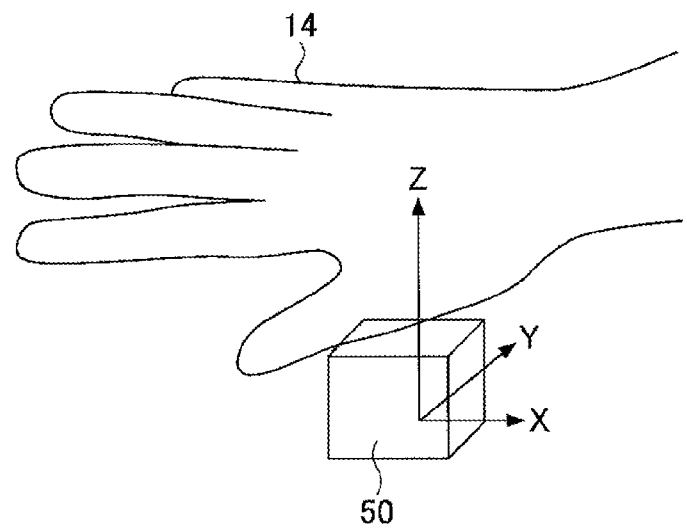
FIGS. 6A-6B are schematic views illustrating an example of obtaining biometric information.
Figure 6B:
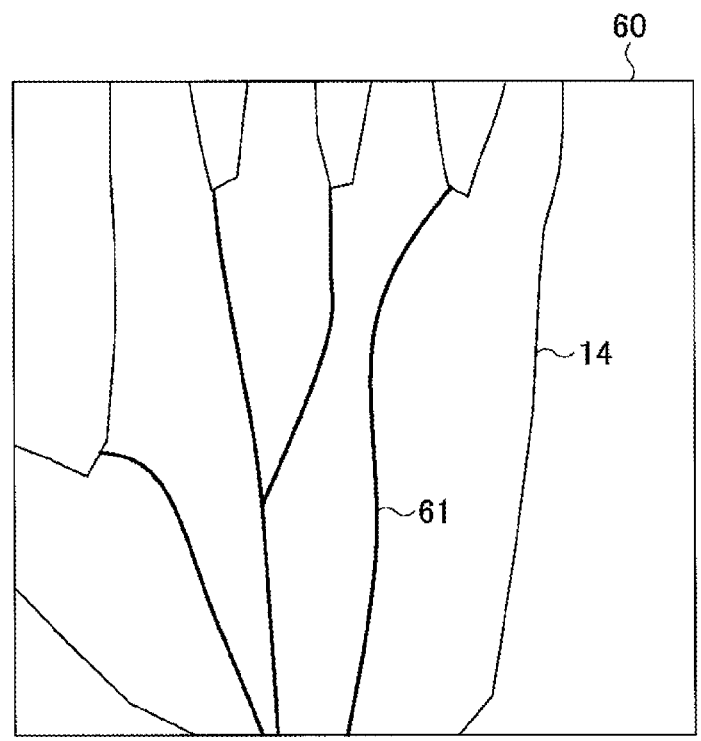

First, an example of obtaining biometric information using the illuminating section 21 and the image capturing section 22 will be described using FIGS. 6A-6B. FIGS. 6A-6B are schematic views illustrating an example of obtaining biometric information. FIG. 6A illustrates an example of an image capturing method, and FIG. 6B illustrates an example of an image of veins obtained as an image capturing result.

In the example in FIG. 6A, an image capturing unit 50 is illustrated in which the illuminating section 21 and the image capturing section 22 are unified. In FIG. 6A, a user hold the hand over the image capturing unit 50 having the palm 14 directed downwards, but it is not limited to this.

Near infrared light emitted by the illuminating section 21 of the image capturing unit 50 illuminates the palm 14, and strength distribution of the reflected light, transmitted light or the like is obtained by the image capturing section 22 of the image capturing unit 50. Using the obtained captured image, an image of veins can be extracted by the extracting section 24. Although an image of veins is obtained as biometric information according to the first embodiment, it is not limited to this, but other biometric information (for example, a fingerprint) or the like may be obtained.

As illustrated in the example in FIG. 6B, an image of internal veins (blood vessels) 61 of the palm 14 is captured in the image 60. The image 60 is a two-dimensional array including a number of pixels, and each of the pixels has a value (pixel value) corresponding to strength of light. The image size is, for example, 100×100 pixels or the like, but not limited to this. Coordinate values of the image correspond to the X-Y coordinate values (x, y) in FIG. 6A.

<Pliable Part Detecting Section 23>

Figure 7:
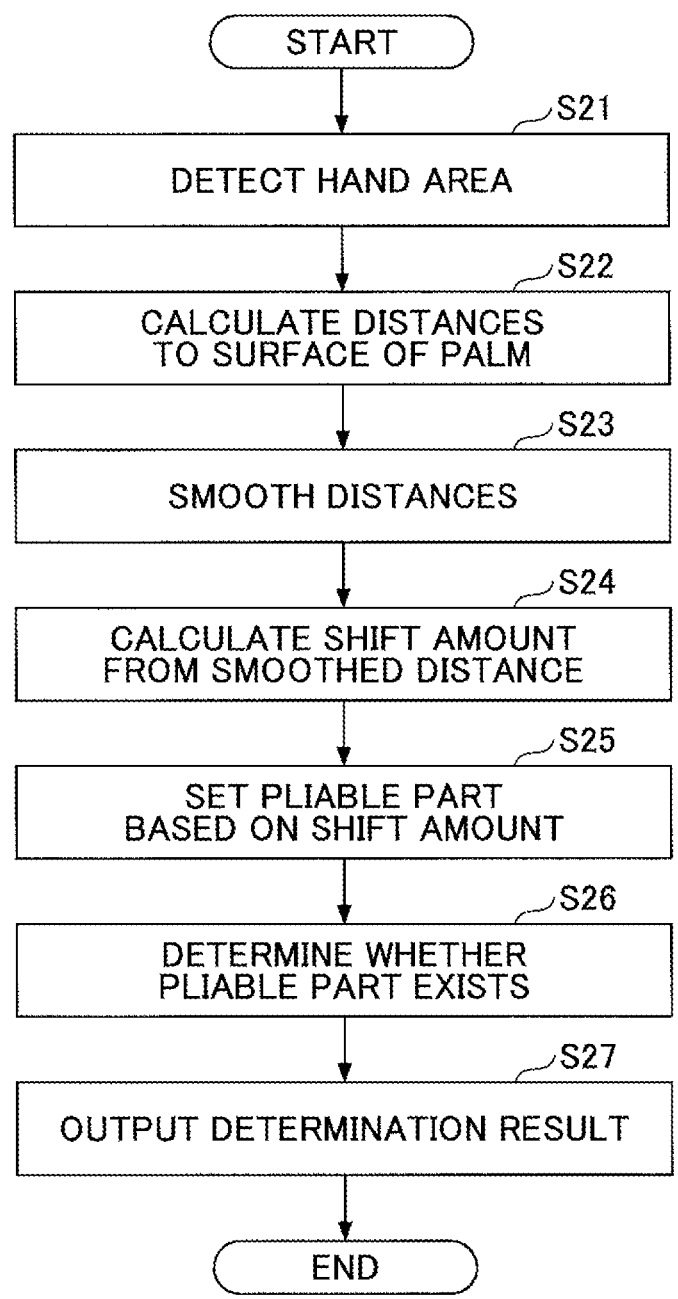
FIG. 7 is a flowchart illustrating an example of a pliable part detection procedure.

Next, an example of pliable part detection by the pliable part detecting section 23 will be described. FIG. 7 is a flowchart illustrating an example of a pliable part detection procedure. Also, FIGS. 8A-8F are schematic views illustrating an example of images generated at steps of the pliable part detection procedure.

In the pliable part detection procedure illustrated in the example in FIG. 7, the pliable part detecting section 23 detects a hand area in the image captured by the image capturing section 22 (Step S21). Next, the pliable part detecting section 23 calculates distances from the image capturing section 22 (for example, the center of a camera) to the surface of the palm (the Z-coordinate values in FIG. 6A) at points on the hand area (Step S22). Also, at Step 22, the pliable part detecting section 23 smoothes the distances to the surface of the palm using the distance values calculated at Step S22 (Step S23). Smoothing of the distances is, for example, obtaining an average of the distances at the points on the hand area obtained at Step S22, but not limited to this, and it may be, for example, an average of the distances at points in a specific part of the hand area set beforehand.

Next, the pliable part detecting section 23 calculates an amount of shift from the smoothed distance using a difference between the distance at each of the points in the hand area obtained at Step S22 and the smoothed distance obtained at Step S23 (Step S24), and based on the calculated amount of shift, sets pliable parts (Step S25).

Next, the pliable part detecting section 23 determines whether there is a pliable part actually on the pliable parts obtained at Step S25 (Step S26), and outputs a determination result (Step S27).

<S21: Detection of Hand Area>

Next, an example of detecting a hand area at Step S21 described above will be described concretely. According to the first embodiment, not only a hand area, but also an image of veins may be extracted together. For example, an image captured by the image capturing section 22 has a bright background, a comparatively dark hand area, and a darker pattern of veins. Therefore, a hand area can be detected by applying a threshold value procedure to the captured image for the pixel values representing shading (for example, brightness information) as follows.

For example, the pliable part detecting section 23 provides an image representing a hand area and an image representing veins, sets the upper left pixel with the coordinate values of (x, y)=(0, 0) as a pixel of interest. Next, if the pixel value of the pixel of interest is greater than a first threshold value set beforehand, the pliable part detecting section 23 determines that it is a pixel in the background, and sets the pixel value of 0 to the pixel of interest in both of the images.

Also, if the pixel value is less than or equal to the first threshold value and greater than a second threshold value set beforehand (assuming first threshold value>second threshold value), the pliable part detecting section 23 determines that it is a pixel in the hand area, and sets the pixel value of 1 to the pixel of interest in the image representing the hand area and the pixel value of 0 to the pixel of interest in the image representing veins. Further, if the pixel value is less than or equal to the second threshold value, the pliable part detecting section 23 determines that it is a pixel in the veins, and sets the pixel value of 1 to the pixel of interest in both of the images representing the hand area and the image representing veins. This is because veins are parts of the hand area.

The pliable part detecting section 23 executes Step S21 as described above for all of the pixels by moving the pixel of interest to detect a hand area.

Figure 8A:
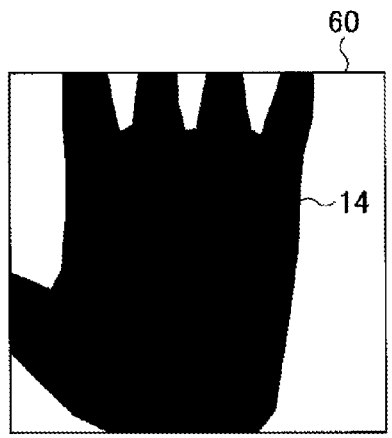
FIGS. 8A-8F are schematic views illustrating an example of images generated at steps of a pliable part detection procedure.

The first threshold value described above is set to a value less than an average pixel value in the background. If the pixel value ranges from 0 to 255, for example, the value of 150 may be used. Also, the second threshold value is set to be less than the first threshold value. Also, the second threshold value is set to a value greater than an average pixel value in an image of veins (for example, the value of 60 or the like). As a result, the image 60 of a hand area is detected as illustrated in FIG. 8A. Here, in the example in FIG. 8A, pixels whose values are less than or equal to the first threshold value described above is illustrated in black.

<S22: Example of Calculation of Distance to Surface of Palm>

Next, an example of calculation of the distance to the surface of a palm 14 described above at Step S22 will be described concretely. The distance from the image capturing section 22 to the surface of a palm 14 described above, for example, can be calculated based on shading of a captured image. This is based on a principle that a brighter pixel has a shorter distance with respect to the surface of a palm on which light is projected. A method based on this principle is disclosed, for example, in "Shape-from-shading: a survey", Ruo Zhang, Ping-Sing Tsai, James Edwin Cryer and Mubarak Shah, IEEE Trans. on PAMI, Vol. 21, No. 8, pp. 690-706, 1999", and the like.

Here, denoting the coordinate values of a pixel included in a captured image by $(u, v)$, and the coordinate values of a point on the surface of a palm by $(x, y, z)$ from which the pixel is projected, the distance $d$ from the origin to the point is represented by $d=\sqrt{(x^2+y^2+z^2)}$. For example, if an image is captured by a perspective projection, and if the origin of the image is taken on an optical axis center of the image capturing section 22, the origin of the three-dimensional coordinate system is taken at the projection center of the image capturing section 22, and the optical axis is selected as the z-axis, then, $u=f(x/z)$ and $v=f(y/z)$ are satisfied.

Here, f represents a focal distance measured by units of pixel length. Also, f may be set to a value defined when designing the optical system of the image capturing unit 50, or may be obtained with calibration before operation. The distance $d$ to the surface of a palm is equal to $(\sqrt{(u^2+v^2+f^2)}) \cdot (z/f)$. With the method described above, d or z can be obtained for each pixel $(u, v)$. Therefore, using the formula described above, the pliable part detecting section 23 can obtained the coordinate value $(x, y, z)$ of a point on the surface of a palm from which a pixel $(u, v)$ is projected.

Figure 8B:
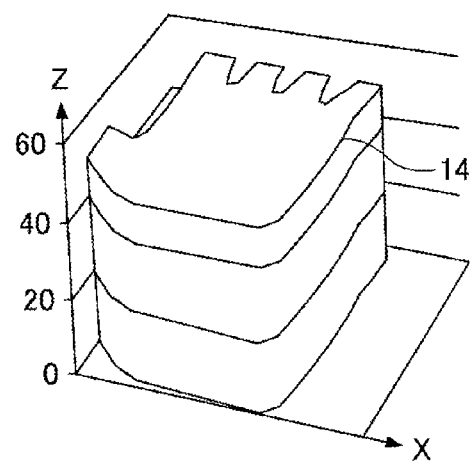

FIG. 8B is a schematic view illustrating a three-dimensional graph representing the surface of a palm with the obtained coordinate values of $(x, y, z)$. In the example in FIG. 8B, the unit of length in the z-axis is one mm. In the example in FIG. 8, a hand is held 50 mm above the image capturing unit 50 to calculate the distance to the surface of the palm. A part other than the hand area is illustrated with z=0.

<S23: Smoothing of Distance>

Next, smoothing of the distance at Step S23 described above will be described concretely. As a method of smoothing the distance to the surface of a palm, for example, there is a simple average method that averages distances to pixels included in a neighborhood in a hand area. The size of a neighboring area may be set to, for example, a typical size of a pliable part (for example, five pixels), but it is not limited to this. Also, the method described above has a problem in that it may be influenced by a slope of a hand as a whole.

Therefore, as a smoothing method that excludes the influence of a slope of a hand as a whole, there is a method, for example, that approximates the surface of a palm by a plane. In the following example, a plane approximation method based on the least squares method will be described.

First, $(x_i, y_i, z_i)$ $(i=1, \ldots, n)$ denote the coordinate values of points on the surface of a palm. Also, $ax+by+cz=d$ denotes the equation of a plane to be obtained. The distance between the plane and a point $(x_i, y_i, z_i)$ is given by $|ax_i+by_i+cz_i-d|/\sqrt{(a^2+b^2+c^2)}$.

Therefore, the sum of squares of the distances of all points is represented by the following formula (1).

$$J(a, b, c, d) = \sum_{i=1}^{n} \frac{(ax_i + by_i + cz_i - d)^2}{a^2 + b^2 + c^2} \quad (1)$$

The solution is a set of plane parameters a, b, c and d with which the formula takes the minimum value. The parameters a, b, c and d can be obtained by differentiating J in formula (1) with a, b, c and d, respectively, and equating the obtained equations to 0, and solving them.

For example, $(a, b, c)^T$ can be obtained as an eigenvector corresponding to a minimum eigenvalue of a 3×3 positive semi-definite symmetric matrix M. Here, T represents a transpose of a vector. Also, d is $ax'+by'+cz'$. Here, x', y' and z' represent the average values of $x_i$, $y_i$ and $z_i$, respectively. At this moment, the matrix M is given by the following formula (2).

$$M = \sum_{i=1}^{n} \begin{pmatrix} x_i - x' \\ y_i - y' \\ z_i - z' \end{pmatrix} (x_i - x', y_i - y', z_i - z') \quad (2)$$

Calculating M for the example in FIG. 8B, the following formula (3) is obtained.

$$M = \begin{pmatrix} * & * & 0 \\ * & * & 0 \\ 0 & 0 & 0 \end{pmatrix} \quad (3)$$

Here, an * in formula (3) described above represents a certain real number whose value is not specified because it does not have an influence on the following calculation. Also, the eigenvalue λ and the eigenvector x of the positive semi-definite symmetric matrix M are defined as a non-negative real number and a non-zero column vector that satisfy $Mx=\lambda x$. Here, $\lambda=0$ and $x=(0, 0, 1)^T$ satisfy the condition, hence they are an eigenvalue and an eigenvector of M, respectively. Further, the eigenvalue 0 happens to be the minimum eigenvalue among the eigenvalues of M. Thus, a=0, b=0, and c=1 are obtained. Also, d=50 is obtained because z'=50. Therefore, the equation of the plane to be obtained is z=50.

Also, the pliable part detecting section 23 may adopt another smoothing method, for example, that uses a predetermined curved surface set beforehand instead of a plane as described above, to be fitted for smoothing the distance. Also, the pliable part detecting section 23, for example, may obtain a typical hand form beforehand that is to be translated, enlarged, or reduced for obtaining a smoothed hand form having the most matching distances to the surface of a palm.

<S24: Calculation of Shift>

Next, calculation of a shift at Step S24 described above will be described concretely. At Step S24, an amount of shift is calculated from a difference between a distance at a point in a hand area and the smoothed distance obtained at Step S23.

For example, if the pliable part detecting section 23 uses the plane approximation method for approximating the surface of a palm as a smoothing method, a shift is calculated by obtaining the distance to the plane. Denoting the equation of a plane as ax+by+cz=d, the distance between the plane and a point $(x_i, y_i, z_i)$ is given by $|ax_i+by_i+cz_i-d|/\sqrt{(a^2+b^2+c^2)}$.

For example, for FIG. 8B described above, the difference with the smoothed distance described above is 0 at every point in the hand area because $z_i$=50, a=0, b=0, c=1, and d=50.

<S25: Setting of Pliable Part>

Next, an example of setting of pliable parts at Step S25 described above will be described concretely. As a setting method of pliable parts, for example, a pixel that is determined to have a shift value greater than a threshold value at Step S24 may be set as a pliable part, but it is not limited to this.

The threshold value described above, for example, may be set to a typical calculation error difference of a shift (for example, 3 mm) as a reference.

An area is set as a pliable part, for example, if the number of pixels in the area or the area itself is greater than a threshold value (for example, 1% of the overall hand area). Detection of a pliable part means that a pliable part is generated. Also, the pliable part detecting section 23 determines that no pliable part is detected (a pliable part is not generated) if the number of pixels (or area) constituting a pliable part is less than the threshold value set beforehand.

For example, if the pliable part detecting section 23 sets a pliable part using the calculation result illustrated in FIG. 8B, there are no pixels to be included in a pliable part when comparing with the threshold value of 3 mm described above, hence there are no pliable parts. Therefore, the pliable part detecting section 23 can determine that no pliable part is generated.

<Example of Images of Veins and Pliable Part>

Figure 8C:
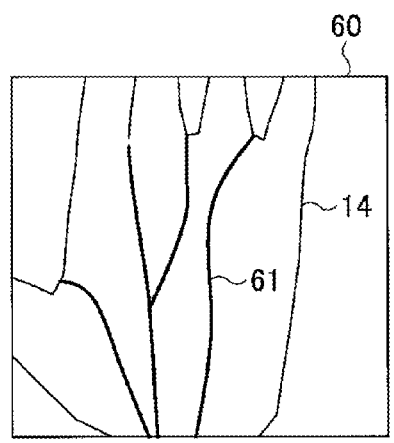
Figure 8D:
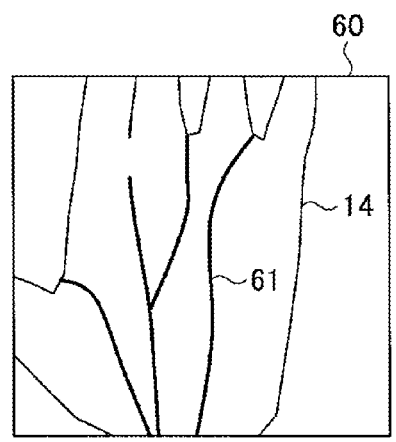

Here, FIGS. 8C-8D are first and second image examples illustrating images of veins extracted by the extracting section 24. The image size of the image 60 in FIGS. 8C-8D is 100× 100 pixels or the like, similarly to the one in FIG. 6B described above, but it is not limited to this. In the images 60 in FIGS. 8C-8D, dark locations in the captured images of a palm 14 when illuminated by near infrared light are illustrated in black.

Figure 8E:
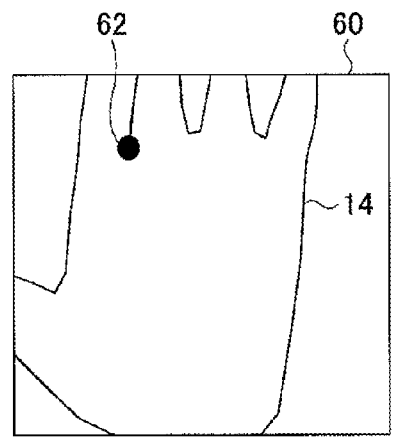
Figure 8F:
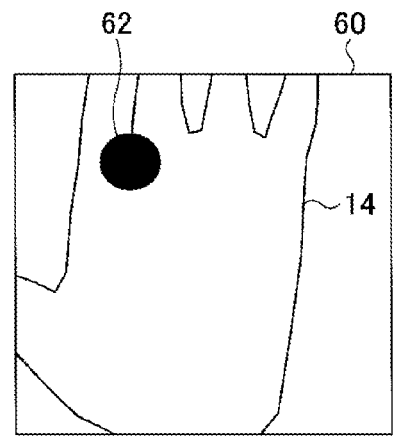

Also, FIGS. 8E-8F correspond to FIGS. 8C-8D, respectively, in which the images 60 are illustrated with respective pliable parts in the hand forms. In FIGS. 8E-8F, the pliable parts 62 are found around the joining part of the index finger and the middle finger of the hand 14. Suppose that, for example, the pliable part in the example in FIG. 8E occupies 0.5% of the overall hand area, and the pliable part in the example in FIG. 8F occupies 1.5% of the overall hand area. In this case, if the threshold value is set to 1% as described above, the pliable part detecting section 23 determines that a pliable part is not generated in the captured image 60 in FIG. 8E, and determines that a pliable part is generated in the captured image 60 in FIG. 8F.

Here, in the captured image 60 in FIG. 8C, the image of veins 61 has little difference when compared with the image of veins 61 in FIG. 6B because there is a very little pliable part. On the other hand, the image of veins 61 in FIG. 8D lacks a part (pliable part) of veins. Therefore, for example, if the image of veins 61 in FIG. 6B is used as registered data for authentication, and the images of veins 61 in FIGS. 8C-8D are captured as data to be verified, authentication succeeds with FIG. 8C, and fails with FIG. 8D. Therefore, according to the present embodiment, an opening posture of fingers of a hand 14 of a user is detected based on a result of pliable part detection described above to execute control for guiding the user to open the palm more if the fingers are not sufficiently opened.

<Extracting Section 24>

Figure 9:
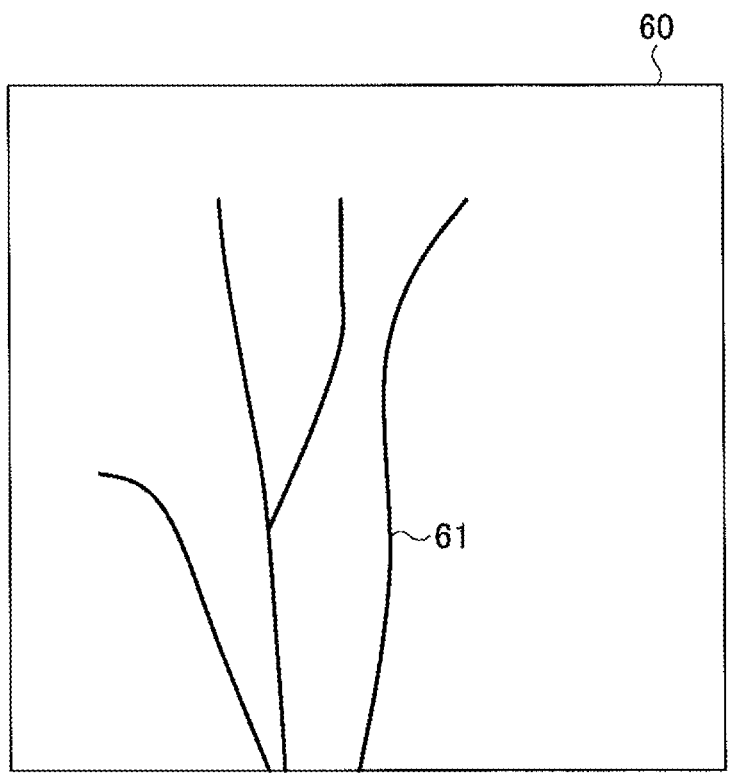
FIG. 9 is a schematic view illustrating an example of an extracted image of veins.

Next, an example of an image of veins extracted by the extracting section 24 described above will be described concretely. FIG. 9 is a schematic view illustrating an example of an extracted image of veins. In the example in FIG. 9, a part corresponding to the image of veins 61 (value "1") in the image 60 captured by the image capturing section 22 is illustrated in black.

With the extracting method according to the first embodiment, the image of veins 61 can be represented as a binary-valued image, but it is not limited to this. For example, for reducing a memory capacity or for speeding up verification, only characteristic values of an image of veins 61 in a captured image may be extracted to calculate a degree of similarity to registered data by comparing with the characteristic values for authentication. As for characteristic values, for example, coordinate values of points constituting an image of veins, or vertices of broken lines obtained by a broken line approximation of an image of veins with thin lines, coordinate values of characteristic points such as branch points, endpoints, and the like, but not limited to these.

<Concrete Example of Registered Data>

Next, a concrete example of registered data stored into the storage section 35 will be described. Registered data is stored into the storage section 35 in which a user ID is associated with an image of veins for identifying the user.

Registered data is stored into the storage section 35 with a predetermined format, for example, "user ID (0001): image of veins (0, 0, 1, 1, 1, 1, 0, 1, 1, . . . )",
"user ID (0002): image of veins (0, 0, 0, 1, 1, 1, 1, 0, 0, . . . )",
and so on. Data of an image of veins described above, for example, is converted into a string of digits based on a certain rule. Data of an image of veins may be, for example, a string of data represented by "0" and "1" obtained when scanning pixels of a binary-valued image in a predetermined order, but it is not limited to this. Here, "0" represents a part other than an image of veins, and "1" represents a part of an image of veins.

Also, the information stored in the storage section 35 is not limited to these, but may include, for example, verification results and user information other than the ID, and the like.

<Verifying Section 32>

Next, the verifying section 32 in the authentication apparatus 12 will be described concretely. If an image of veins is represented, for example, as a binary-valued image, the verifying section 32 calculates a degree of similarity with the following method.

For example, the verifying section 32 sets a pixel of interest at the upper left corner (coordinate value (x, y)=(0, 0)) of an obtained image of veins (data to be verified) in a captured image, and an image of veins (registered data) stored in the storage section 35 beforehand, respectively, provides a first variable (counter) for holding the number of matched pixels, and a second variable (counter) for holding the number of pixels constituting the image of veins, and initializes the variables to 0. Here, it is assumed that the sizes of the captured image and the image stored beforehand are the same (for example, 100×100 pixels).

Next, the verifying section 32 compares pixel values of the pixel of interest. The verifying section 32 increases the value of the first variable by one if both of the pixels are a part of the image of veins, respectively. Also, the verifying section 32 increases the value of the second variable by one if one of the pixels is a part of the image of veins.

Next, the verifying section 32 compares pixels at the same position in the images for all pixels by moving the pixel of interest one by one, respectively, and after completing comparison of all the pixels, divides the first variable by the second variable to set the quotient as the degree of similarity. Here, verification of an image of veins may be done by comparing the images of veins with each other as described above.

A value obtained by the method of calculating a degree of similarity described above may be influenced by the position and/or direction where a hand of a user is placed. Therefore, to reduce such an influence, the verifying section 32, for example, calculates a degree of similarity repeatedly with a shift between the pixels to be compared in the registered data and the data to be verified, to use the maximum value among the obtained degrees of similarity.

<Determining Section 33>

Next, the determining section 33 will be described concretely. The determining section 33 compares the degree of similarity calculated at the verifying section 32 and a threshold value Th defined beforehand, for example, and determines a person in question is one of the registered persons if the degree of similarity is greater than the threshold value Th.

The determining section 33, for example, collects biometric information of a considerable number of people for an evaluation purpose, calculates a false acceptance rate (a rate of false authentication in that data to be verified of a person in question falsely coincides with the registered data) with the collected biometric information and various threshold values, and examines the threshold values to obtain a false acceptance rate of 1/10000 (the same precision as four-digit personal identification number) to obtain a threshold value Th to be used. Also, the determining section 33 may set a predetermined threshold value (for example, 90%) or the like, but it is not limited to this.

<Modified Examples>

As a modified example of the first embodiment described above, for example, when executing pliable part detection, the pliable part detecting procedure may be switched depending on the size of a pliable part. For example, the pliable part detecting section 23 may output coordinate values (x, y) of pixels constituting a pliable part to the verifying section 32 if the pliable part is smaller than a predetermined threshold value (for example, 2% of a hand area). The verifying section 32 calculates the degree of similarity using an image of veins having pixels corresponding to the obtained coordinate values removed.

Also, the pliable part detecting section 23 may indicate to the user to open the palm more with an error message or the like on the display section 27, for example, if a pliable part is greater than the predetermined threshold value (for example, 2% of a hand area) described above, and capture an image again. Here, the pliable part detecting section 23 may flash a lamp or output sound with a buzzer in addition to the error message. A method of verifying characteristic points having specific pixels removed is disclosed in, for example, Japanese Laid-open Patent Publication No. 2002-329205 and the like, but not limited to this.

The modified example is applicable, for example, to the image of veins 61 illustrated in FIG. 8D with which verification is executed having the pixels in the pliable part removed because the pliable part is 1.5% of the overall hand area as illustrated in FIG. 8F. The image of veins in the captured image illustrated in FIG. 8D is substantially the same as the image of veins in the captured image illustrated in FIG. 6B except for the pliable part. Therefore, if the image of veins in the captured image illustrated in FIG. 8D is data to be verified and the image of veins in the captured image illustrated in FIG. 6B is the registered data, the degree of similarity is obtained that is close to the maximum value of 1 by verification, and authentication succeeds. With such a switched procedure, authentication can be executed even if there is a little pliable part in a palm, which improves convenience.

Here, the method that has a part removed from an image of veins to be authenticated may make it harder to distinguish the image from images of veins of other people, and lead to a higher false acceptance rate because the amount of information (area) used for verification is reduced. Therefore, it is preferable to set the threshold value for the pliable part to an appropriate value taking both convenience and a false acceptance rate into consideration. For example, it is preferable to determine a threshold value by collecting biometric information of a considerable number of people for an evaluation purpose, calculating a false acceptance rate with the collected biometric information and various threshold value, setting a maximum threshold value in the threshold values with a false acceptance rate of lower than 1/10000 (the same precision as four-digit personal identification number), but it is not limited to this. In this way, authentication precision can be improved better than a method, for example, that executes verification using a part of a hand area set beforehand without pliable part detection, because the false acceptance rate can be adjusted within a certain range.

In the first embodiment described above, the threshold value used for pliable part determination may be changed per user. For example, if a user ID is received for authentication, an upper limit value of a pliable part (for example, represented with a ratio to the hand area) for a user obtained at registration may be set to the threshold value. In this way, appropriate authentication can be executed, for example, for a user prone to forming a pliable part by adjusting the sensitivity of pliable part detection.

<Second Embodiment of Biometric Information Input Authentication System>

Figure 10:
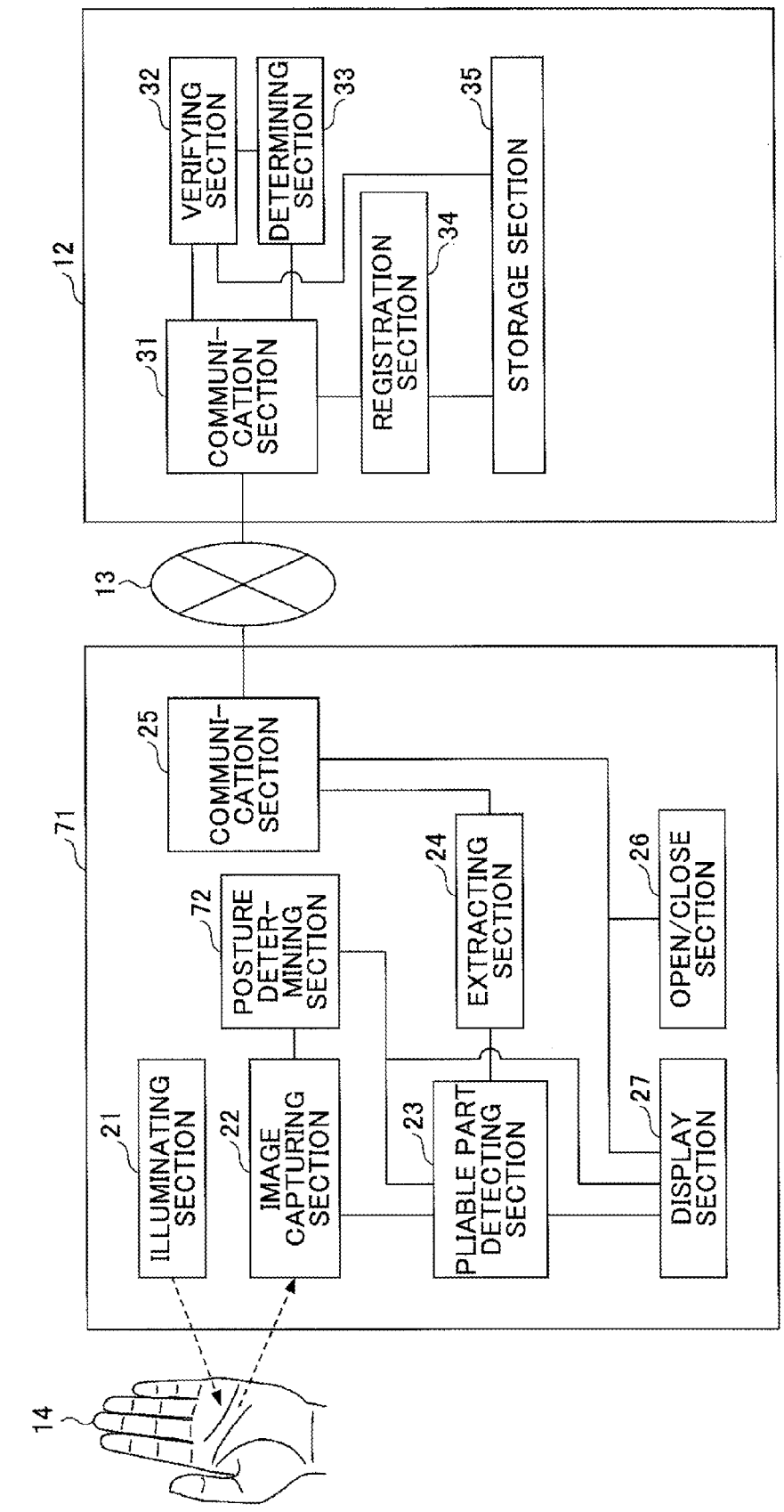
FIG. 10 is a schematic view illustrating an example of a biometric information input authentication system according to a second embodiment.

Next, an authentication system will be described with reference to the drawings according to another embodiment that is different from the embodiment described above. FIG. 10 is a schematic view illustrating an example of a biometric information input authentication system 70 according to a second embodiment.

In the biometric information input authentication system 70, elements having the same functions as in the biometric information input authentication system 10 illustrated in FIG. 1 described above are assigned the same numerical codes, and their concrete description is omitted. In the second embodiment, an authentication system is taken as an example as in the first embodiment that manages entering and leaving of a user by opening or closing a door of a predetermined room or a facility based on an authentication result.

The biometric information input authentication system 70 illustrated in FIG. 10 includes a biometric information input apparatus 71 and an authentication apparatus 12, where the biometric information input apparatus 71 and the authentication apparatus 12 are connected with each other via a communication network 13 so that they are in a state in which data can be transmitted and received.

Compared with the biometric information input apparatus 11 described above, the biometric information input apparatus 71 includes a posture determining section 72 according to the second embodiment. The posture determining section 72 determines a posture of a palm 14.

The posture determining section 72, for example, determines whether the posture of a palm 14 in an image obtained by the image capturing section 22 is appropriate for the pliable part detection procedure, and if it not appropriate, displays an error message on the display section 27 to the user. Also, the display section 27 displays a message for instructing a correction of the posture of the palm 14 to the user to capture an image again.

Also, if the posture is determined as appropriate for the pliable part detection procedure by posture determination, the posture determining section 72 outputs information obtained from the image capturing section 22 to the pliable part detecting section 23.

A hardware configuration according to the second embodiment may be substantially the same as in the first embodiment described above, and concrete description is omitted here.

<Example of Biometric Information Input Procedure in the Second Embodiment>

Figure 11:
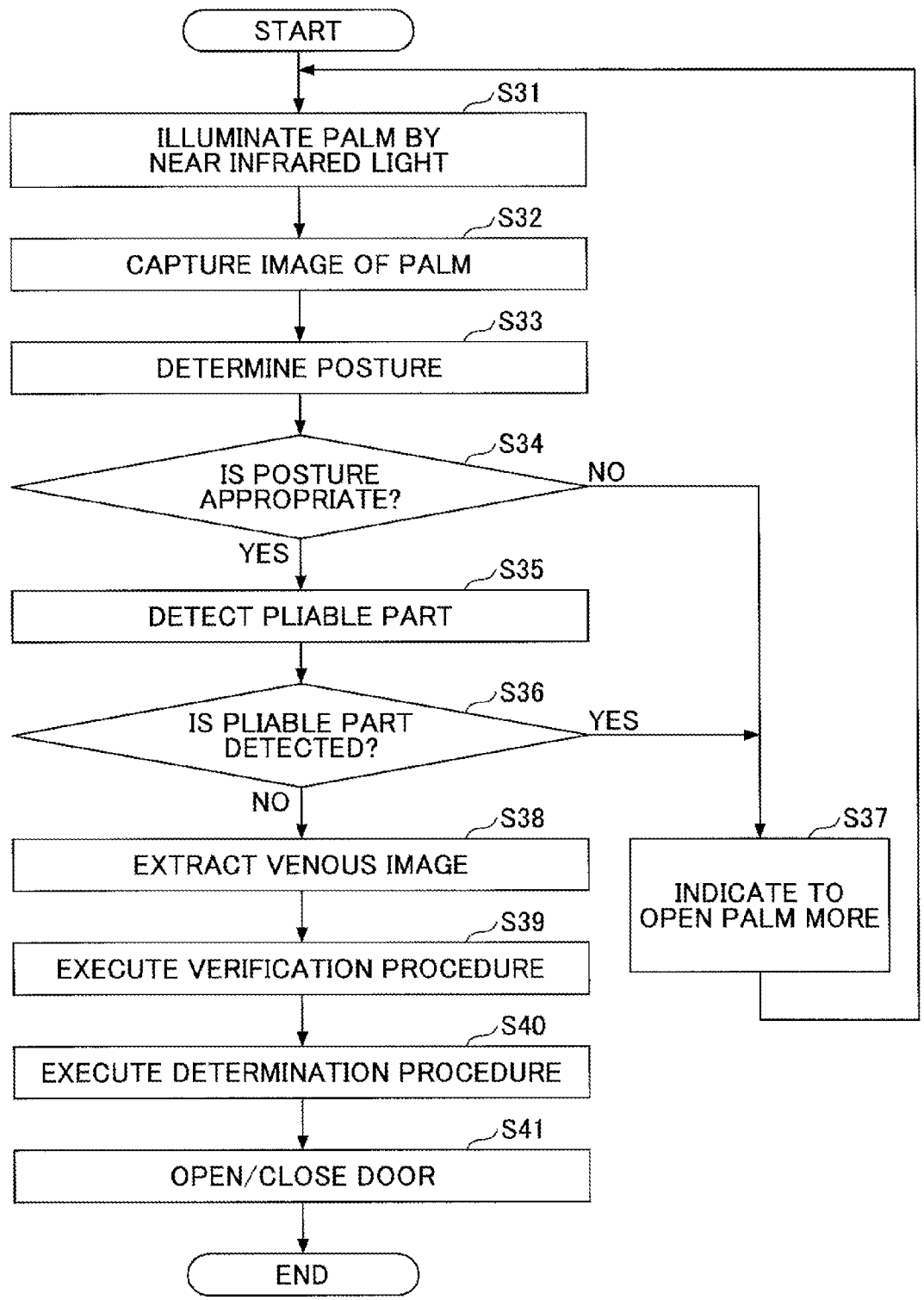
FIG. 11 is a flowchart illustrating an example of a biometric information input procedure according to the second embodiment.

Here, an example of a biometric information input procedure will be described according to the second embodiment using a flowchart. FIG. 11 is the flowchart illustrating an example of the biometric information input procedure according to the second embodiment. Here, a biometric information input procedure illustrated in the example in FIG. 11, as similar to the one in the first embodiment, is a procedure used for the biometric information input authentication system 70 for opening or closing the door, which includes an authentication procedure using biometric information input by the user. Also, in the example in FIG. 11, an image of veins of a hand is assumed as an example of biometric information received as input. Here, the biometric information input procedure illustrated in the example in FIG. 11 is, similarly to the first embodiment, a procedure used for the biometric information input authentication system 70 for opening or closing a door automatically using biometric information input by the user. Also, in the example in FIG. 11, as an example of biometric information received as input, an image of veins of a hand is assumed.

If a user holds the hand over about the illuminating section 21 or the image capturing section 22 of the biometric information input apparatus 11, the illuminating section 21 illuminates near infrared light onto the palm (Step S31). The image capturing section 22 captures an image of the palm illuminated by the near infrared light (Step S32). When capturing an image of the palm at Steps S31 and S32, identification information (ID) of the user may be received by an input section or the like such as an IC card, a keyboard or the like.

Next, the posture determining section 72 determines whether the posture of the hand (Step S33) is appropriate for detecting a pliable part (Step S34). If the posture of the hand is appropriate (S34, YES), the pliable part detecting section 23 detects a pliable part of the palm in the image obtained by the image capturing section 22 (Step S35). Also, the pliable part detecting section 23 determines whether a pliable part is detected (Step S36).

Here, at Step S34, if the posture of the hand is not appropriate (Step S34, NO), the posture determining section 72 indicates to the user to open the palm more with an error message (Step S37) via the display section 27, and the procedure goes back to Step S31 to capture an image again. Also, if the posture of the hand is not appropriate, for example, the posture determining section 72 may flash a lamp or output sound with a buzzer provided in the biometric information input authentication system 70.

Also, if a pliable part is detected (Step S36, YES), the pliable part detecting section 23 indicates to the user to open the palm more with an error message (Step S37) via the display section 27, and the procedure goes back to Step S31 to capture an image again. Here, if a pliable part is detected, the pliable part detecting section 23, for example, may flash a lamp or output sound with a buzzer provided in the biometric information input authentication system 70.

At Step S36, if a pliable part of the palm is not detected (S36, NO), the extracting section 24 extracts an image of veins of the hand (Step S38). The extracted image of veins is transmitted to the authentication apparatus 12 via the communication section 25.

The verifying section 32 of the authentication apparatus 12 executes verification as described above (Step S39). Next, the determining section 33 determines whether authentication succeeds based on the verification result described above (Step S40). The determination result at Step S40 is transmitted to the biometric information input apparatus 11 via the communication section 31. The open/close section 26 of the biometric information input apparatus 11 opens or closes the door based on the determination result obtained at Step S40 (Step S41).

Here, a registration procedure can be executed for registering data in the second embodiment. In this case, similarly to the first embodiment described above, the registration procedure is executed by the registration section 34 instead of Steps S39 to S41 illustrated in FIG. 11 after an image of veins obtained.

<Example of Postures of Palm>

FIGS. 12A-12E are schematic views illustrating an example of postures of a palm. FIG. 12A illustrates a state in which a palm is flat and fingers and the thumb are open. This state is an appropriate posture for inputting an image of veins. Also, FIG. 12B illustrates a state in which the thumb hides the other fingers (called a "self-hidden state", hereafter). Also, FIG. 12C illustrates a state in which adjacent fingers contact with each other (called a "closed-fingers state with thumb", hereafter). Also, FIG. 12D illustrates another closed-fingers state without the thumb. Also, FIG. 12E illustrates a state in which the fingers are hanging downwards that forms a hollow palm (called a "dropped-fingers state", hereafter).

When determining the posture of a palm, the posture determining section 72 executes the following procedure, for example. The posture determining section 72 first determines whether the hand captured by the image capturing section 22 is in a self-hidden state illustrated in FIG. 12B, and determines it is not appropriate for pliable part detection if it is in the self-hidden state.

Second, the posture determining section 72 determines whether it is a closed-fingers state illustrated in FIG. 12C or 12D, and if it is in the closed-fingers state, and determines that is appropriate for the pliable part detection procedure, and outputs the positions of the joining fingers.

Third, the posture determining section 72 determines whether it is a dropped-fingers state, and if it is in the dropped-fingers state, determines that it is appropriate for the pliable part detection procedure, and output the base positions of the dropped fingers.

If no positive determination is obtained for the above first to third determinations, the posture determining section 72 determines that it is appropriate for the pliable part detection procedure, outputs a result that indicates an appropriate opening posture, and ends the procedure. Here, the determination method is not limited to the method described above. For example, the posture determining section 72 may take the position and direction of a palm into consideration. For example, Patent Document 1 discloses a method of detecting the position and direction of a palm. The posture determining section 72 determines that it is not appropriate for pliable part detection if the position and direction is out of a range set beforehand.

<Determination Example of Self-Hidden>

Next, an example of a self-hidden state determined by the posture determining section 72 will be described concretely. For example, the posture determining section 72 obtains the distance from each of the pixels in the image captured by the image capturing section 22 to the surface of the palm from which the pixel is projected. For example, the posture determining section 72 can obtain the distance corresponding to shading information of each of the pixels, but not limited to this. Also, the posture determining section 72 smoothes the obtained distances to the surface of a palm. Smoothing is, for example, obtaining the average of the distances of the multiple pixels included in the surface of a palm, but it is not limited to this. The range of pixels for smoothing is, for example, set to a width of a typical finger (for example, 10 pixels), but it is not limited to this.

The posture determining section 72 calculates a shift from the calculated smoothed distance, and calculates the number of pixels whose shifts are greater than a threshold value (an expected lower limit value of the thickness of a finger, for example, 10 mm). If the number is greater than a threshold value (an expected lower limit value of the area of the finger, for example, 5% of a hand area or the like), the posture determining section 72 determines that it is a self-hidden state.

<Determination Example of Closed Fingers>

Next, an example of closed fingers determined by the posture determining section 72 will be described concretely. A closed-fingers state is determined by detecting joining parts around the base of the fingers. Here, a joining part around the base of the fingers is, for example, a web between the fingers, but it is not limited to this.

The posture determining section 72 detects joining parts of the fingers by the following method. Here, in the following description, the fingers included in a captured image are positioned in the upper part of the image. The posture determining section 72 scans the image downwards from each of the pixels at the upper end of the image, and sets the value of a pixel to 0 if it represents the background and to 1 if it represents the hand area based on shading (brightness information) or the like. Further, the posture determining section 72 changes the value of a pixel into 2 at which the value changes from 0 to 1, namely from the background to the hand area, during the downward scanning of the image, to indicate the pixel as a candidate joining part of the fingers. The posture determining section 72 executes the above procedure to all of the pixels by moving the pixel of interest one by one.

Next, the posture determining section 72 scans all of the pixels in the image one by one, and if it finds a pixel whose value is 2 that represents the candidate joining part, examines the left and right pixels to check whether their values are 1, and if the values are both 1 that represents the hand area, changes the value of 2 that represents a candidate joining part into the value of 3 that represent an actual joining part. With the procedure described above, the posture determining section 72 can obtain the image in which the joining parts of the fingers are identified.

Also, the posture determining section 72 may store coordinate values of pixels that represent the joining parts of the fingers into an array. For example, the posture determining section 72 provides an array for storing coordinate values and a variable (counter) for storing the number of points, which is initialized to 0. Next, the posture determining section 72 scans the image described above, and if there is a pixel whose value is 3 that represents a joining part of the fingers, records the coordinate values into the array, and increases the value of the variable storing the number of points by one.

Figure 13A:
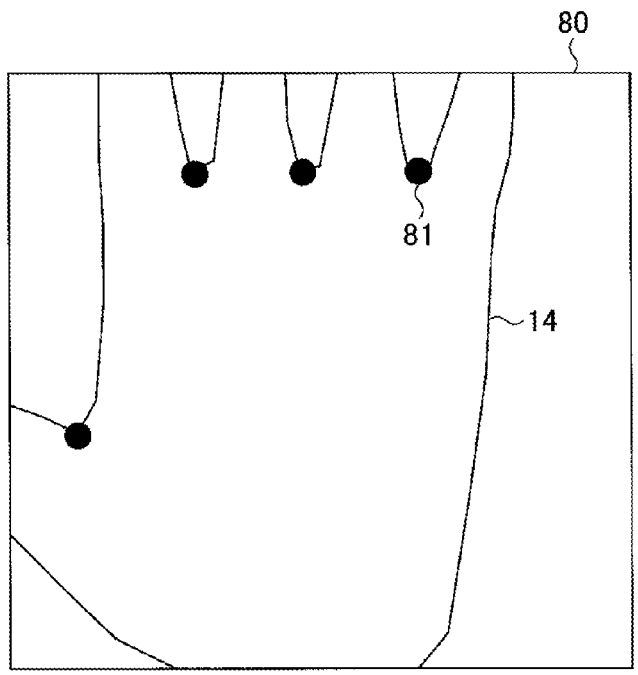
FIG. 13A-13B are schematic views illustrating an example of images of joining parts of fingers.
Figure 13B:
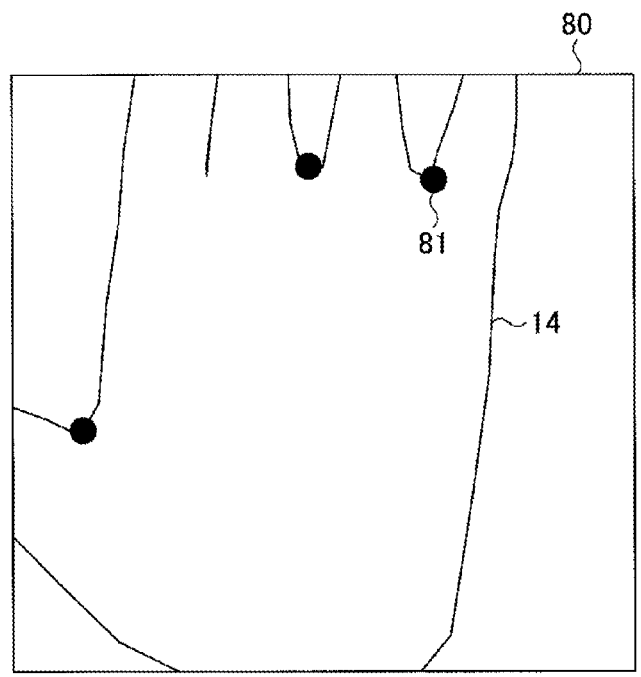

FIGS. 13A-13B are schematic views illustrating an example of images of joining parts of fingers. Here, FIG. 13A illustrates an image 80 of the joining parts of the fingers corresponding to the image 60 in FIG. 6B, and FIG. 13B illustrates an image 80 of the joining parts of the fingers corresponding to the image 60 in FIG. 8C. FIGS. 13A-13B includes tables of coordinate values (horizontal coordinate values and vertical coordinate values), respectively. The coordinate values assume a coordinate system in which the origin (0, 0) is set to the upper left corner of the image, and positive directions are taken rightwards and downwards.

In the examples in FIGS. 13A-13B, pixels having the value of 3 are highlighted with black circles, but pixels having the value of 2 are omitted.

The posture determining section 72 determines that the fingers are not closed if the number of joining parts of the fingers is four or more when detecting closed fingers based on the joining parts, and ends detecting closed fingers. Also, if the number of joining parts is less than four, the posture determining section 72 calculates the average of vertical coordinate values of the pixels included in the hand area, and if the undermost joining part in the image is below the average, it treats the undermost joining part as the joining part of the thumb, and determines that the thumb is not closed.

If no joining part other than that of the thumb is found, the posture determining section 72 determines that the four fingers are all closed, and ends detecting closed fingers. If a joining part other than that of the thumb is found, the posture determining section 72 obtains the horizontal coordinate values of the leftmost and rightmost pixels of the hand area, divides a range defined with both ends into five partitions, and associates each of the joining parts with one of the equally splitting points that has the closest horizontal coordinate value relative to the joining part.

At this moment, if the joining part of the thumb is found, three equally splitting points without an equally splitting point closest to the joining part of the thumb are used for associating with the joining parts. If the joining part of the thumb is not found, three equally splitting points from the left are used for a trial association, and three equally splitting points from the right are also used for another trial association, then one of the trial associations with a smaller error difference (the total of distances between an equally splitting point and a joining part in the horizontal direction) is adopted.

This makes it possible for the posture determining section 72 to determine whether it is the left hand or the right hand. Also, the posture determining section 72 determines that a pair of fingers is closed if their joining part is not associated with one of the equally splitting points.

For example, the posture determining section 72 determines that the fingers are not closed because the number of joining parts 81 is four for the image 80 illustrated in FIG. 13A. Also, the posture determining section 72 determines that some fingers are closed because the number of joining parts 81 is three for the image 80 illustrated in FIG. 13B. As the average of the vertical coordinate values of the hand area is about 50, the undermost joining part in the image (coordinate values of (10, 59)) is associated with the joining part of the thumb because it is below the average. Also, the horizontal coordinate value of the left end is zero and the right end is 80 for the hand area.

Therefore, by horizontally dividing the hand area into five partitions, the horizontal coordinate values of the equally splitting points are turned out to be 16, 32, 48, and 64. However, the joining part of the thumb is found at the left side of the image, the horizontal coordinate values to be used are 32, 48, and 64.

Here, in the example in FIG. 13B, the equally splitting points with the horizontal coordinate values of 48 and 64 are associated with the joining parts. Therefore, the posture determining section 72 can determine that the index finger and the middle fingers are closed because the equally splitting point with the horizontal coordinate value of 32 is not associated with one of the joining parts of the fingers.

<Other Examples of Determination of Closed Fingers>

As another example of determination of closed fingers, for example, the joining parts may be detected when registering data, and the detection result may be stored into the storage section 35 with a user ID. This makes it possible for the posture determining section 72 to compare a detection result of the joining parts of a user stored in the storage section 35 associated with the user ID, with a detection result of joining parts of the user obtained at authentication, and to identify a joining part that is not detected at the authentication, which indicates that the two fingers at the joining part are closed. Here, when comparing the detected joining parts, the posture determining section 72 may associate the detected joining parts with each other that are positioned close enough to each other, and determine that a joining part is not detected if it has no associated joining part.

<Determination Example Of Dropped Fingers>

Next, an example of dropped fingers determined by the posture determining section 72 will be described concretely. Usually, it is very rare that closed fingers and dropped fingers occur at the same time. Therefore, as described above, if closed fingers are detected, dropped fingers are not detected according to the second embodiment. Therefore, when detecting dropped fingers, it is assumed that the four joining parts of the fingers has been detected.

The posture determining section 72 obtains the distance from each of the pixels in the image captured by the image capturing section 22 to the surface of the palm. For example, the posture determining section 72 obtains the distance to the surface of the palm based on the shading of the captured image. Next, the posture determining section 72 groups together pixels corresponding to a finger for each of the fingers, by connecting the pixels corresponding to the left end of the hand area, the right end of the hand area, and the joining parts of the fingers with broken lines. Here, the vertical positions of the left end and the right end are set to the vertical positions of the adjacent joining parts of the fingers, respectively. Pixels of the palm without the fingers are also put into a group.

For each of the groups representing respective fingers, the posture determining section 72 obtains the average of the distances to the surface of the palm. The posture determining section 72 also obtains the average distance and standard deviation for the group representing the palm area without the fingers. The posture determining section 72 determines that the posture of the hand is in a dropped-fingers state if the average distance to the fingers is less than the average distance of the palm area without the fingers by more than the standard deviation.

<Another Example of Determination of Dropped Fingers>

As another example of determination of dropped fingers, for example, the average distance to the surface of the hand may be obtained for each of the fingers when registering data, and the detection result may be stored into the storage section 35 with a user ID. This makes it possible for the posture determining section 72 to read the average value of the distance for the user ID from the storage section 35 when executing authentication, with which the average value of the distance to the surface of the palm to be verified is compared to determine dropped fingers.

As a method of comparing with the average value of the distance on registration, for example, a difference to the average value may be calculated for each finger. If the differences are greater than a predetermined threshold value (for example, 3 mm), it may be determined as dropped fingers, but it is not limited to this.

<Pliable Part Detecting Section 23>

Next, the pliable part detecting section 23 will be described according to the second embodiment. According to the second embodiment, the pliable part detecting section 23 can detect a pliable part more securely by obtaining the posture of an opening palm by the posture determining section 72.

The pliable part detecting section 23 can execute detection of a pliable part only on areas set as candidate pliable parts where there is a possibility of pliable part generation depending on the posture of the opening hand. Also, the pliable part detecting section 23 may simply execute detection of a pliable part as done in the first embodiment, then set an area where a pliable part is detected as a candidate pliable part.

Figures 14, 15:
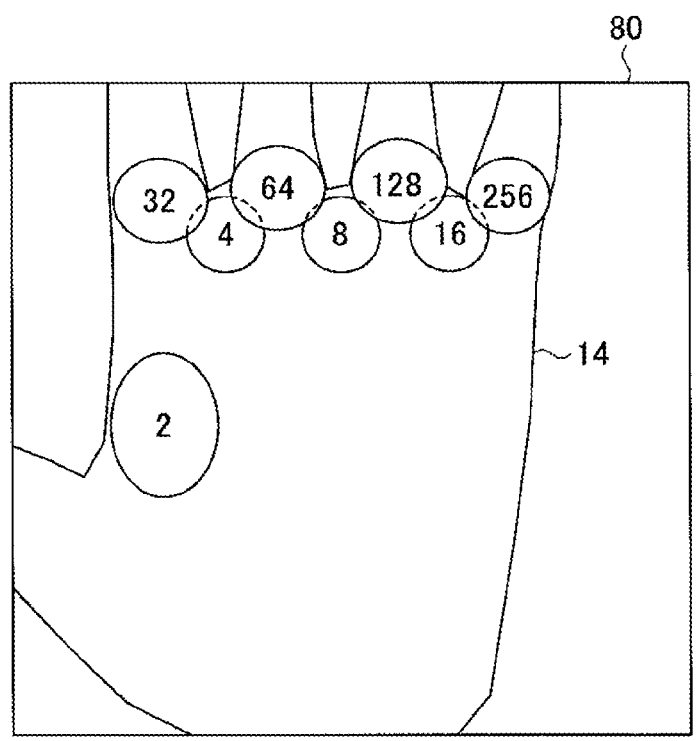
FIG. 14 is a schematic view illustrating an example of candidate pliable parts.
FIG. 15 is a schematic view illustrating an example of an image of a typical hand form designated with candidate pliable parts.

FIG. 14 is a schematic view illustrating examples of candidate pliable parts. In the examples illustrated in FIG. 14 where a relationship between postures of an opening hand and candidate pliable parts are described, if the posture of an opening hand is in a closed-fingers state with the closed thumb, the index finger side of the thenar may be set to a candidate pliable part. If the posture of an opening hand is in a closed-fingers state without the thumb, the joining parts of the closed fingers may be set to a candidate pliable part. Also, if the posture of an opening hand is in a dropped-fingers state, the base of dropped fingers may be set to a candidate pliable part. Here, examples of candidate pliable parts are not limited to those illustrated in FIG. 14.

FIG. 15 is a schematic view illustrating an example of an image of a typical hand form designated with candidate pliable parts. The pliable part detecting section 23 provides an image to be output, and initializes it to zero. Next, the pliable part detecting section 23 provides an image representing the typical hand form beforehand for the left hand and the right hand. Pixels corresponding to the background are set with the value 0, pixels corresponding to a hand are set with the value 1, pixels corresponding to the index finger side of the thenar are set with the value of 2, pixels corresponding to the joining parts of the fingers are set with the values of 4, 8, and 16, respectively, and pixels corresponding to the base of the fingers are set with the values of 32, 64, 128, and 256, respectively. At this moment, multiple writes may be done for one pixel.

Next, the pliable part detecting section 23 generates a correspondence between the form of the hand area obtained from the captured image and the typical hand form. The correspondence may be generated so that the centers and the widths in the vertical and horizontal directions of both of the hand forms are coincident with each other by applying translation and/or enlargement or reduction to the hand forms. Also, the pliable part detecting section 23 may convert the typical hand form so that the joining parts of the fingers are coincident with each other as much as possible.

Next, the pliable part detecting section 23 extracts values contained in the image of the typical hand form that correspond to the detected opening hand posture, and writes the extracted values into the output image as illustrated in FIG. 15. In the image 80 illustrated in FIG. 15, pixels values of candidate pliable parts included in the palm 14 are represented by strings of digits. Here, in the example in FIG. 15, the candidate pliable parts are illustrated greater than the actual area for displaying the strings.

The pliable part detecting section 23 sets candidate pliable parts based on the form of the surface of the palm 14, and executes detection of a pliable part only for the set candidate pliable parts, which makes the processing time shorter than when detecting a pliable part all over the palm.

Figure 16:
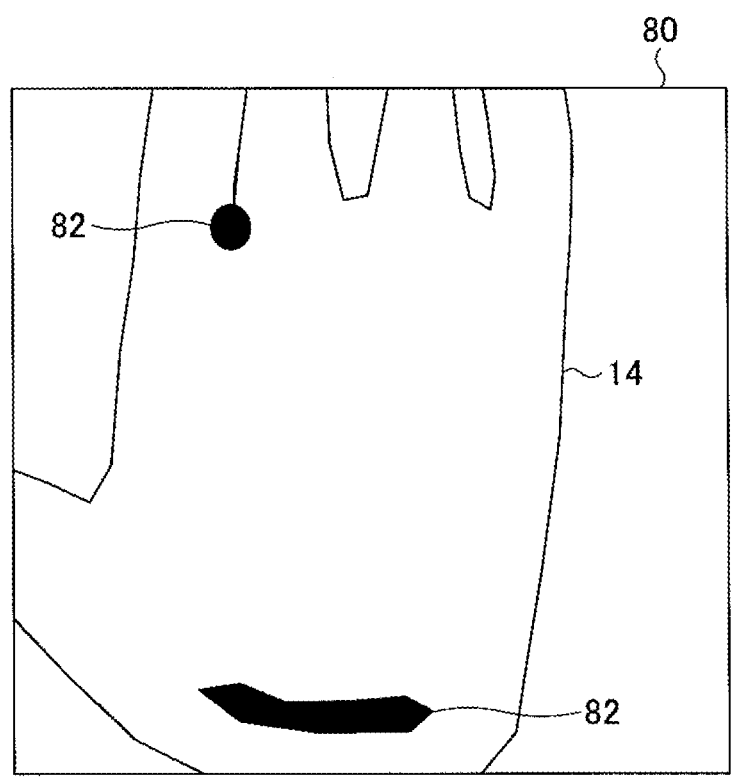
FIG. 16 is a schematic view illustrating a difference between the first embodiment and the second embodiment.

FIG. 16 is a schematic view illustrating a difference between the first embodiment and the second embodiment. The image 80 illustrated in FIG. 16 includes a pliable part 82 in a palm 14, which is detected by pliable part detection by the pliable part detecting section 23. In the image 80 in FIG. 16, another pliable part 82 is detected in the neighborhood of a wrist, which makes the total of the pliable parts 82 occupies 2.5% of the overall hand area.

Here, if the threshold value is set to 1% of the overall hand area for determining whether there is a pliable part, it is determined that there is a pliable part for this case according to the first embodiment, which is indicated to the user to open the palm. On the other hand, according to the second embodiment, the posture determining section 72 described above determines that the index finger and the middle finger are closed in the image in FIG. 16. Therefore, pliable part detection is executed only in the neighbor of the joining part of these fingers. Consequently, the pliable part is detected as in FIG. 8E, which results in a smaller pliable part that amounts 0.5% of the overall hand area.

Therefore, the same captured image is determined that there is no pliable part according to the second embodiment, to which verification is applied. For example, if the image of veins illustrated in FIG. 6B is registered data, and the image of veins corresponding to FIG. 16 is data to be verified, the images of veins are determined as substantially the same by verification, and authentication succeeds.

Here, comparing the method of verification that always excludes pixels in the candidate pliable part area with reference to the posture of an opening hand with the method according to the second embodiment, although they have substantially the same level of convenience, the method according to the second embodiment has better authentication accuracy. Here, the second embodiment can be modified as described in the modified examples of the first embodiment.

Also, the threshold values used for pliable part determination may be changed by taking the thickness and/or size of fingers of a user into consideration. For example, the pliable part detecting section 23 may collect biometric information of a considerable number of people for an evaluation purpose in advance, detect the base of fingers of a hand for each piece of the collected biometric information to obtain thicknesses and sizes of the fingers, and classify the pieces of the biometric information into multiple classes based on the thicknesses and sizes of the fingers. Also, the pliable part detecting section 23 may obtain statistical distribution of pliable parts (for example, ratios to a hand area) for each of the classified classes for defining the threshold value for pliable part determination. As the threshold value, for example, the sum of the average and the standard deviation of the area of each of the classes may be used. This makes it possible to have pliable part detection less affected by the thickness or size of fingers.

The first and second embodiments may be combined appropriately. Also, according to the above embodiments, although biometric information is input and authenticated for opening and closing a door, it is not limited to this, but may be applied to user authentication for an automated teller machine (ATM) at a bank and the like.

According to the above embodiments, biometric information can be input conveniently and appropriately. Also, authentication can be done if a palm does not open sufficiently, as long as a pliable part is not generated. This reduces restrictions on the posture of an opening palm for authentication, which makes it convenient. Also, according to the above embodiments, pliable parts are identified based on a positional relationship of fingers for executing pliable part detection on those parts, which makes the processing time shorter than when detecting a pliable part all over the palm.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A biometric information input apparatus comprising:
   an image capturing camera device configured to obtain a captured image of a biological object;
   a memory device configured to store a program; and
   a central processing unit configured to execute the program to perform:
   obtaining distances between a position of an image capturing camera device and a plurality of points on a surface of a biological object from an image captured by the image capturing camera device to calculate an average value of the obtained distances;
   comparing each of the obtained distances with the calculated average value of the obtained distances to detect whether there is a pliable part on the surface of the biological object; and
   extracting biometric information from the captured image if the pliable part is not detected.

2. The biometric information input apparatus as claimed in claim 1, wherein the central processing unit is configured to execute the program to calculate the average value of the obtained distances by smoothing the obtained distances, and detects the pliable part based on an amount of shift between the calculated average value and each of the obtained distances.

3. The biometric information input apparatus as claimed in claim 1, wherein the central processing unit is configured to execute the program to display a message indicating that the pliable part is detected if an area of the pliable part on the surface of the biological object is greater than a predetermined threshold value.

4. The biometric information input apparatus as claimed in claim 3, wherein the displayed message includes positional information of the detected pliable part.

5. The biometric information input apparatus as claimed in claim 1, wherein the central processing unit is configured to execute the program to determine whether to detect whether there is a pliable part, based on a posture of the surface of the biological object obtained from the captured image obtained by the image capturing camera device.

6. The biometric information input apparatus as claimed in claim 1, wherein the central processing unit is configured to execute the program to set a candidate pliable part from a form of the surface of the biological object, and detect whether there is a pliable part on the set candidate pliable part.

7. The biometric information input apparatus as claimed in claim 1, wherein the central processing unit is configured to execute the program to execute authentication using the extracted biometric information.

8. A non-transitory computer-readable recording medium having a program stored therein for causing a computer to execute a biometric information input method, the method comprising:
- capturing a captured image of a biological object with an image capturing camera device;
- obtaining distances between a position of the image capturing camera device and a plurality of points on a surface of the biological object from the captured image to calculate an average value of the obtained distances;
- comparing each of the obtained distances with the calculated average value of the obtained distances to detect whether there is a pliable part on the surface of the biological object; and
- extracting biometric information from the captured image if the pliable part is not detected.

9. A biometric information input method comprising:
- capturing a captured image of a biological object with an image capturing camera device;
- obtaining distances between a position of the image capturing camera device and a plurality of points on a surface of the biological object from the captured image to calculate an average value of the obtained distances;
- comparing each of the obtained distances with the calculated average value of the obtained distances to detect whether there is a pliable part on the surface of the biological object based on comparison of each of the obtained distances with an average value of the obtained distances; and
- extracting biometric information from the captured image if the pliable part is not detected.

* * * * *